United States Patent [19]

Mintz et al.

[11] Patent Number: 5,744,453
[45] Date of Patent: Apr. 28, 1998

[54] POLYAMINE CONJUGATES FOR TREATMENT OF INFECTION

[76] Inventors: Clifford S. Mintz, 6 Pebble Rd., East Windsor, N.J. 08570; Natan A. Kogan, 38-B Cedar Lake, Highland Park, N.J. 08904; Ramesh Kakarla, 111B Taylor Ave., East Brunswick, N.J. 08816; Helena R. Axelrod, 15 Piedmont Dr., Cranbury, N.J. 08512; Michael J. Sofia, 3 Holly La., Lawrenceville, N.J. 08658

[21] Appl. No.: 583,809

[22] Filed: Jan. 5, 1996

[51] Int. Cl.$^6$ .......................... A61K 31/21; A61K 31/16; A61K 31/13

[52] U.S. Cl. ...................... 514/26; 514/579; 514/613; 514/659; 514/182; 514/169; 552/502; 536/5; 536/6.1

[58] Field of Search ...................... 514/579, 510, 514/613, 659, 26, 182, 169; 536/5, 6.1; 552/502

[56] References Cited

U.S. PATENT DOCUMENTS

| | | | |
|---|---|---|---|
| 5,338,837 | 8/1994 | Kahne | 536/5 |
| 5,455,335 | 10/1995 | Kahne | 536/5 |
| 5,627,270 | 5/1997 | Kahne | 536/5 |

FOREIGN PATENT DOCUMENTS

WO95/29186  11/1995  WIPO .

OTHER PUBLICATIONS

Moore, K. S. "Squalamine: An Aminosterol from the Shark", *Proc. Nat'l. Acad. Sci.* (1993) 90:1354–1358.

Vaara, M. "Agents that Increase the Permeability of the Outer Membrane", *Microbil. Rev.* (1992) 56:395–411.

Varra, M. "Sentization of Gram–negative Bacteria to Antibiotics and Complement by Non–toxic Oligopeptides", *Nature* (1983) 303:526–528.

Sandownik, A. et al. "Rapid Construction of a Squalamine Mimic", *J. Am. Chem. Soc.* (1995) 117:6138–6139.

Bellini, A.M. et al., "Antimicrobial Activity of cholane Compounds: cholic and Deoxycholic Acid Derivatives", *Eur. J. Med. Chem* (1983) 18(2):185–190.

Bellini, A.M. et al., "Antimicrobial Activity of Cholane Compounds: Cheno and Ursodeoxycholic Acid Derivatives", *Eur. J. Med. Chem* (1983) 18(2):191–195.

*Primary Examiner*—C. Warren Ivy
*Assistant Examiner*—D. Margaret M. Mach
*Attorney, Agent, or Firm*—Lowe, Price, LeBlanc & Becker

[57] ABSTRACT

The present invention relates to methods of preventing or treating an infection or disease caused by an infectious agent. The present invention also relates to the augmentation of the efficacy of existing anti-infective agents by the co-administration of the compounds described herein.

27 Claims, 10 Drawing Sheets

(spermine)

(spermidine)

(n = 1-10)

(n = 1-10)

(n = 0-10)

(guanidine)

(n = 0 - 10; R=H or poly(aminoalkylene))

POLYAMINE CONJUGATES FOR TREATMENT OF INFECTION

FIELD OF THE INVENTION

The present invention relates to a novel method for treatment of an infection, especially bacterial or fungal, comprising administering an effective amount of the disclosed compounds to a patient or host in need thereof.

BACKGROUND OF THE INVENTION

Few developments in the history of medicine have had such a profound effect upon human life and society as the development of the power to control infections due to microorganisms.

Although true antibiotics were recognized in folk medicine as long as 2500 years ago when the Chinese reported the medicinally beneficial effects of moldy bean curd, it was not until the nineteenth century when Pasteur founded the science of bacteriology that these substances were studied systematically. Since that time, the pace of new discoveries has accelerated with many new and important antibiotics belonging to various groups of compounds being discovered in the nineteenth century.

Although several thousand antibiotics are known, only a relative handful have reached the market and achieved commercial importance. Only a very few, perhaps 0.3% of the many antibiotics mentioned in the scientific literature, are now used in medicine and agriculture. A continuing need exists, therefore, for selective and effective antibiotics that do not easily produce resistance, show an absence of toxicity to the kidney, liver and central nervous system and which are easily administered in oral or parenteral forms. The present invention addresses this need and other needs.

SUMMARY OF THE INVENTION

The present invention relates to a novel method for the treatment or prevention of an infection comprising administering to a host or subject in need thereof an effective amount of a compound or its salt represented by formula (I)

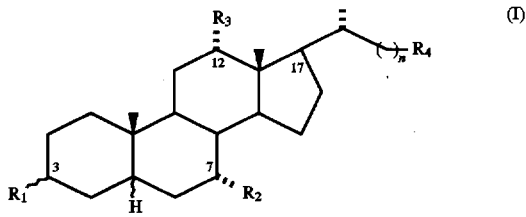

(I)

in which $R_1$ can be an H, OH, $OR_5$, $NH_2$, $NHR_6$, or $NR_6R_7$;

$R_2$ and $R_3$ may be the same or different and can be an H, OH, or $OR_5$;

$R_4$ can be $CONH_2$, $CONHR_6$, $CONR_6R_7$, $CH_2NH_2$, $CH_2NHR_6$, $CH_2NR_6R_7$, $CO_2$—Y—$NH_2$, $CO_2$—Y—$NHR_6$, or $CO_2$—Y—$NR_6R_7$;

$R_5$ is a protected or unprotected glycosyl moiety comprising 1–10 monosaccharide units in which the glycosidic linkage at the anomeric carbon atom of each monosaccharide unit is independently alpha or beta;

$NH_2$, NHR, and $NR_5R_7$ represent an unsubstituted amino group, a monosubstituted amino group and a disubstituted amino group, respectively, in which $R_6$ and $R_7$ may be the same or different and represent a hydrocarbon group comprising 1–15 carbon atoms substituted with one or more unsubstituted, monosubstituted, or disubstituted amino groups;

Y represents a linear or branched alkylene group comprising 1–10 carbon atoms;

n is an integer from 0–10.

The present inventors have surprisingly and unexpectedly discovered that the compounds represented by the formula (I) possess antibiotic activity against a wide variety of microorganisms, and may therefore be used, for example, to prevent or treat bacterial or fungal infections in animals, particularly humans, as well as to serve as disinfectants for suppressing bacterial or fungal growth, for example, on surfaces such as those of surgical instruments.

The inventors have also found that the antibiotic compounds useful in the present method also augment the activity of certain other antibiotic compounds, including conventional ones, such that much less of such other antibiotic compounds is required to suppress bacterial or fungal growth.

Other aspects of the present invention will become apparent to those of ordinary skill in the art upon further consideration of the detailed description of the preferred embodiments, presented below, which are meant to illustrate the basic concepts of the invention.

DETAILED DESCRIPTION OF THE INVENTION

The present invention is broadly concerned with a novel method for treatment of an infection comprising administering to a host or subject in need thereof an effective amount of certain compounds represented by formula (I)

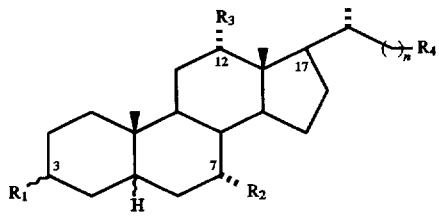

in which $R_1$ can be an H, OH, $OR_5$, $NH_2$, $NHR_6$ or $NR_6R_7$; $R_2$ and $R_3$ may be the same or different and can be an H, OH or $OR_5$; $R_4$ can be $CONH_2$, $CONHR_6$, $CONR_6R_7$, $CH_2NH_2$, $CH_2NHR_6$, $CH_2NR_6R_7$, $CO_2$—Y—$NH_2$, $CO_2$—Y—$NHR_.$, or $CO_2$—Y—$NR_6R_7$; $R_5$ is a protected or unprotected glycosyl moiety comprising 1–10 monosaccharide units in which the glycosidic linkage at the anomeric carbon atom of each monosaccharide unit is independently alpha or beta; $NH_2$, $NHR_6$, and $NR_6R_7$ represent an unsubstituted amino group, monosubstituted amino groups, and a disubstituted amino group, respectively, in which $R_6$ and $R_7$ may be the same or different and represent a linear, branched or cyclic hydrocarbon group (e.g., an aliphatic group, a cyclic aliphatic group, an aromatic group or combinations of same) comprising 1–15 carbon atoms optionally substituted with one or more unsubstituted, monosubstituted or disubstituted amino groups; Y represents a linear or branched alkylene group comprising 1–10 carbon atoms; n is an integer from 0–10, preferably 0–3; or its salts.

The degree of substitution of the amino group is determined by the number of bonds to hydrogen emanating from the amino group. Thus, an unsubstituted amino group has two N—H bonds (e.g., —$CH_2$—$CH_2$—$NH_2$). A monosubstituted amino group has one N—H bond (e.g., —$CH_2$—NH—$CH_2$— or —CH=NH). A disubstituted amino group has none (e.g., =CH—NR—$CH_2$— or —CH=N—CH=). By "substituted with one or more unsubstituted, monosubstituted or disubstituted amino groups" is meant that the hydrocarbon group comprising 1–15 carbon atoms contains at least one amino group either within the hydrocarbon backbone (e.g., —NH—$CH_2$—, —$CH_2$—NR—$CH_2$—, —CH=N—$CH_2$, —CH=N—CH=, and the like) or coming off the backbone (e.g., a primary amine, a secondary amine, a tertiary amine, an imine or the like, such as —$CH_2$—$CH_2$—$NH_2$, —$CH_2$—CH(—$NH_2$)—$CH_2$—, —$CH_2$—CR($NH_2$)—$CH_2$—, —CH=NH or —CR=NH).

Accordingly, such amino groups are capable of accommodating a charge, for example, in protic media (e.g., —$CH_2$—$NH_2^{\oplus}$—$CH_2$— or —$CH_2$—$CH_2$—$NH_3^{\oplus}$) or on formation of a quaternary ammonium salt (e.g., —$CH_2$—$CH_2$—$NMe_3^{\oplus}$, wherein Me stands for methyl). The preferred compounds of the present invention include those that are able to accommodate two or more positive charges. Yet others can accommodate three, four or even more positive charges.

Figure 1:
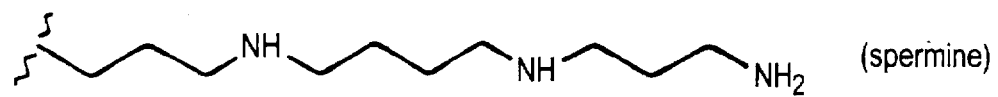
FIG. 1 shows additional examples of aliphatic amine moieties.
Figure 1:
Figure 1:
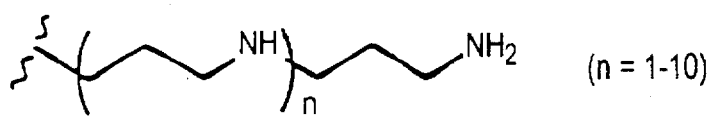
Figure 1:
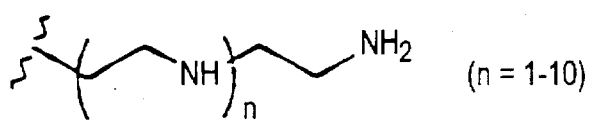
Figure 1:
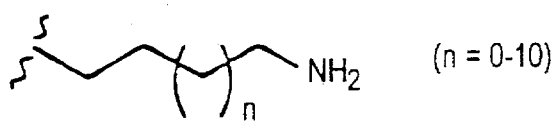
Figure 1:
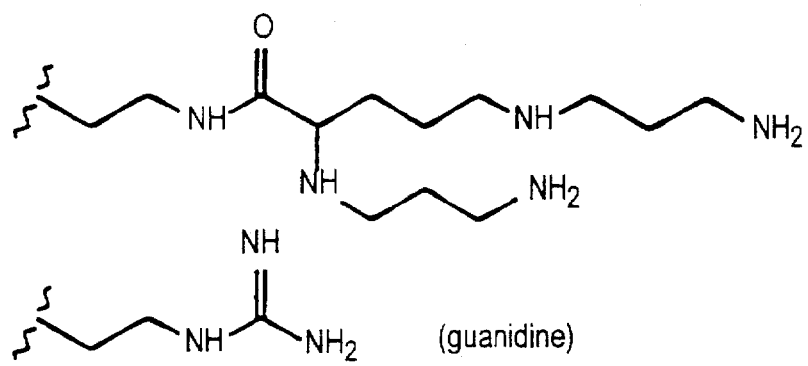
Figure 1:
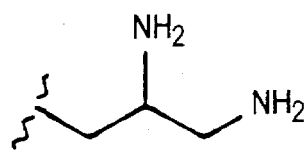
Figure 1:
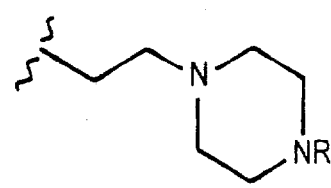
Figure 1:
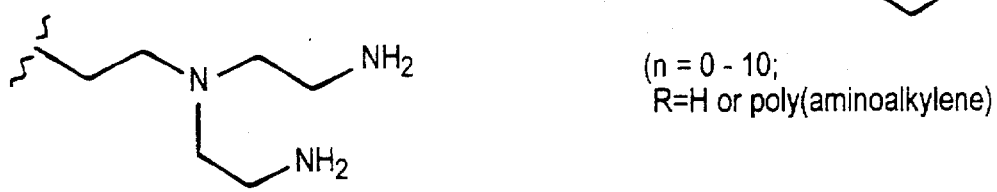
Figure 2:
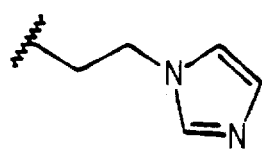
FIG. 2 shows further examples of aromatic amine moieties.
Figure 2:
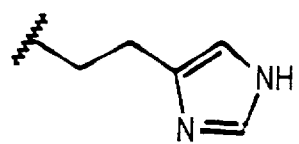
Figure 2:
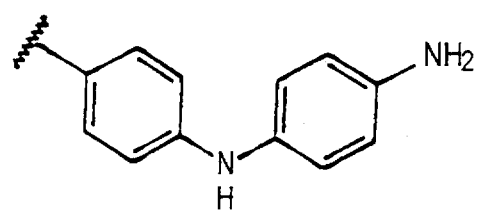
Figure 2:
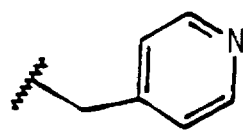
Figure 2:
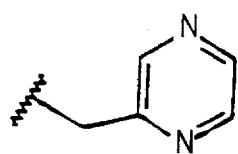
Figure 2:
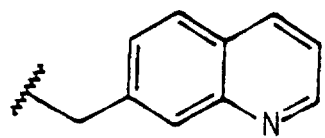
Figure 2:
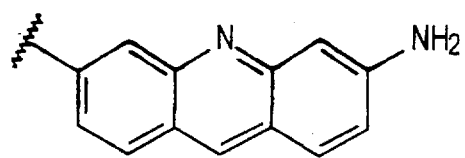

Additional examples of selected amino group-containing moieties, that may be used as $R_6$ and/or $R_7$, can be found in FIGS. 1 and 2.

As stated above, the group $R_5$ can be a protected or unprotected glycosyl moiety, which, in turn, may comprise 1–10 monosaccharide units (e.g., a monosaccharide, a disaccharide, a trisaccharide, etc.). In the present case, the term "monosaccharide" is any sugar residue or derivative thereof. The monosaccharide may, for example, be a hexose (e.g., D-allose, L-allose, D-altrose, L-altrose, D-fucose, L-fucose, D-glucose, L-glucose, D-mannose, L-mannose, D-gulose, L-gulose, D-idose, L-idose, D-galactose, L-galactose, D-rhamnose, L-rhamnose, D-talose, L-talose, and the like, or any deoxy form thereof, e.g., a 2-deoxyhexose, or any amino-substituted derivative thereof, e.g., an aminosugar, such as D-glucosamine, L-glucosamine, D-galactosamine, L-galactosamine, etc.). Furanoses, deoxyfuranoses, amino-substituted furanoses, and the like are also suitable, such as D-ribose, L-ribose, D-arabinose, L-arabinose, D-xylose, L-xylose, D-lyxose, L-lyxose, etc.

Furthermore, the protecting groups for the hydroxyl groups (or amino groups, as the case may be) can be chosen from a wide variety of protecting groups appropriate for a given set of conditions. These protecting groups, the choice of which will be apparent to one skilled in the art, may include, but are not limited to, benzyl, pentenyl, pivaloyl, trimethylsilyl, tert-butyldimethylsilyl, tert-butyldiphenylsilyl, triisopropylsilyl, acetyl, tetrahydropyranyl, benzoyl, $C_1$–$C_3$ alkyl, isopropylidene, benzylidene, trifluoroacetyl, (2-methoxyethoxy)methyl, succinyl, orthoester, paramethoxybenzyl, allyl, and the like.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

In a specific embodiment, the group $R_1$ has the configuration beta. In another, the group $R_1$ has the configuration alpha. In a particular embodiment, at least one of $R_1$, $R_2$, and $R_3$ represents OH. In another embodiment, at least two of $R_1$, $R_2$, and $R_3$ represent OH, and in still another embodiment, all three of $R_1$, $R_2$, and $R_3$ represent OH.

The present invention contemplates all other combinations of the various groups, including, but not limited to, embodiments in which $R_1$ and $R_2$ represent $OR_5$, and $R_3$ represents OH; $R_1$ and $R_3$ represent $OR_5$, and $R_2$ represents OH; or $R_2$ and $R_3$ represent OR, and $R_1$ represents OH.

Furthermore, a method is disclosed wherein $R_6$ together with the nitrogen atom to which it is attached derives from a polyamine. Suitable polyamines include, but are not limited to, alkylene diamines, such as 1,3-diaminopropane, and 1,12-diaminododecane, and biogenic polyamines (that is, those found in nature), such as 1,4-diaminobutane (putrescine), 1,5-diaminopentane (cadaverine), N-(4-aminobutyl)-1,3-diaminopropane (spermidine, an alkylene triamine), and N-[N-(3-aminopropyl)-4-aminobutyl]-1,3-diaminopropane(spermine, an alkylene tetraamine). Other polyamines are also suitable, including but not limited to, tetraethylene-pentamine ("pentamine"), pentaethylenehexamine ("hexamine") and the like, including branched aliphatic polyamines. With unsymmetrical polyamines, the present invention contemplates all other possible points of attachment of the polyamine to the steroid nucleus. For example, in spermidine, any of the three amino groups may be attached to the side chain or at the C-3 position of the steroid nucleus.

In selected embodiments of the present invention, the group $R_1$ or $R_4$ is neither an amino acid nor a peptide.

In especially preferred embodiments of the present invention, the compound is selected from the group wherein n=2 and, $R_1=\alpha$-OH, $R_2$=H, $R_3$=OH and $R_4$=CO-spermine;
$R_1=\alpha$-OH, $R_2$=OH, $R_3$=OH and $R_4$=CO-spermine;
$R_1=\alpha$-OH, $R_2=\alpha$-D-Glc, $R_3=\alpha$-D-Glc and $R_4$=CO-spermine;
$R_1=\alpha$-OH, $R_2$=H, $R_3=\alpha$-D-Glc and $R_4$=CO-spermine;
$R_1=\alpha$-OH, $R_2=\alpha$-D-Glc, $R_3$=H and $R_4$=CO-spermine;
$R_1=\alpha$-OH, $R_2$=H, $R_3$=OH and $R_4$=CO-pentamine;
$R_1=\alpha$-OH, $R_2$=H, $R_3$=OH and $R_4$=CO-hexamine;
$R_1=\alpha$-OH, $R_2$=OH, $R_3$=H and $R_4$=CO-spermine;
$R_1=\alpha$-OH, $R_2$=OH, $R_3$=H and $R_4$=CO-pentamine;
$R_1=\alpha$-OH, $R_2$=OH, $R_3$=OH and $R_4$=CO-pentamine;
$R_1=\alpha$-OH, $R_2$=OH, $R_3$=OH and $R_4$=CO-hexamine;
$R_1=\alpha$-OH, $R_2=\alpha$-D-Glc, $R_3=\alpha$-D-Glc and $R_4$=CO-hexamine;
$R_1=\alpha$-OH, $R_2=\alpha$-D-Glc, $R_3=\alpha$-D-Glc and $R_4$=CO-pentamine; and
$R_1=\alpha$-OH, $R_2$=H, $R_3$=H and $R_4$=CO-hexamine.

Particularly preferred compounds include 3α,12α-dihydroxy-7-deoxy-5β-cholan-24-oic acid, N-(4,9-diaza-12-aminododecyl)amide (Compound A); 3α,7α,12α-trihydroxy-5β-cholan-24-oic acid, N-(4,9-diaza-12-aminododecyl)amide (Compound B); 3α-hydroxy-7α,12α-di(1'α-glucosyl)-5β-cholan-24-oic acid, N-(4,9-diaza-12-aminododecyl)amide (Compound C); 3α-hydroxy-7-deoxy-12α-(1'α-glucosyl)-5β-cholan-24-oic acid, N-(4,9-diaza-12-aminododecyl)amide (Compound D); 3α-hydroxy-12-deoxy-7α-(1'α-glucosyl)-5β-cholan-24-oic acid, N-(4,9-diaza-12-aminododecyl)amide (Compound E); 3α,12α-dihydroxy-7-deoxy-5β-cholan-24-oic acid, N-(3,6,9-triaza-11-aminoundecyl)amide (Compound F); 3α,12α-dihydroxy-7-deoxy-5β-cholan-24-oic acid, N-(3,6,9,12-tetraaza-14-aminotetradecyl)amide (Compound G); 3α,7α-dihydroxy-12-deoxy-5β-cholan-24-oic acid, N-(4,9-diaza-12-aminododecyl)amide (Compound H); 3α,7α-dihydroxy-12-deoxy-5β-cholan-24-oic acid, N-(3,6,9-triaza-11-aminoundecyl)amide (Compound I); 3α,7α,12α-trihydroxy-5β-cholan-24-oic acid, N-(3,6,9-triaza-11-aminoundecyl)amide (Compound J) ; 3α,7α,12α-trihydroxy-12-deoxy-5β-cholan-24-oic acid, N-(3,6,9,12-tetraaza-14-aminotetradecyl)amide (Compound K); 3α-hydroxy-7α,12α-di(1'α-glucosyl)-5β-cholan-24-oic acid, N-(3,6,9,12-tetraaza-14-aminotetradecyl)amide (Compound L); 3α-hydroxy-7α,12α-di(1'α-glucosyl)-5β-cholan-24-oic acid, N-(3,6,9-triaza-11-aminoundecyl)amide (Compound M); and 3α-hydroxy-7,12-dideoxy-5β-cholan-24-oic acid (or lithocholic acid), N-(3,6,9,12-tetraaza-14-aminotetradecyl)amide (Compound N).

It is of course preferred that the compounds have a degree of purity such that they are suitable for use as an anti-infective. Further, the pure or substantially pure compounds are preferably employed in the methods of the present invention. It is understood that one or more compound(s) of the present invention may be employed in any of the methods described herein.

The compounds represented by formula (I) are useful as anti-infective agents, having utility in inhibiting the growth of, including killing, microorganisms. The compounds are particularly useful as broad spectrum antibacterial agents, having activity against both gram-positive and gram-negative bacteria, and as antifungal agents, having activity against yeast, mold, or other types of fungi. Thus, the compounds represented by formula (I) may be employed in utilities suitable for such antimicrobial or antifungal agents.

The compounds represented by formula (I) may, for example, be used in treating a host infected with a bacterium or fungus, or in preventing infection of said host by said bacterium or fungus, comprising the step of administering to the host one or more compounds represented by formula (I) or a pharmaceutically acceptable salt thereof in an amount effective for prevention or treatment. Treatment of such infections according to the present invention includes both mitigation as well as elimination thereof.

Hosts administered the compounds represented by formula (I) may be plants or animals, particularly animals such as dogs, cats and other domestic mammals and, especially humans. The dosage form and mode of administration, as well as the dosage amount, may be selected by one of ordinary skill in the art. The dosage amount will vary with the severity of the infection, and with the size and species of the host. Exemplary daily dosages for an adult human are those within the range of from about 0.001 mg to about 1,000 mg/day, preferably about 0.01 mg to about 500 mg/day, most preferably about 0.1 mg to about 200 mg/day. In certain instances, the preferred ranges may be about 0.5 mg to about 100 mg/day, more preferably about 1 mg to about 25 mg/day, and most preferably, about 1 mg to about 10 mg/day.

In order to use a compound represented by formula (I) in the method for the therapeutic treatment of mammals including humans, in particular in treating infection, it is normally formulated in accordance with standard pharmaceutical practice as a pharmaceutical composition.

The compounds represented by formula (I) may be administered in standard manner for the disease condition that one desires to treat. Administration to a mammalian host may, for example, be oral, topical, rectal or parenteral. Administration to a plant host may be accomplished by, for example, application to seed, foliage or other part of the plant, or to the soil. It may also be sprayed over surfaces and over a wide area to be treated. For these purposes the compounds of this invention may be formulated by means known in the art into the form of, for example, tablets (including lozenges and granules), dragees, pills, ampoules, capsules, aqueous or oily solutions or suspensions, emulsions, dispersible powders, suppositories and sterile injectable aqueous or oily solutions or suspensions.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian.

It should be understood that an effective dose of the compound useful in the present method may vary depending on whether the compound is being administered alone or in combination with a second compound. Generally, the effective dose can decrease if the second compound of a combination also exhibits anti-infective activity, especially those anti-infective agents whose activity is augmented in the presence of the compounds disclosed for use in the invention.

The active agents can also be administered as suspensions, solutions and emulsions of the active compound in aqueous or non-aqueous diluents, syrups, granulates or powders. Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active agent can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, in the presence of a surface-active agent), such as diluents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), polycrystalline cellulose, aluminum methahydroxide, agar-agar and tragacanth, or mixtures thereof.

The pharmaceutical compositions can also contain bulking agents and preservatives, as well as perfumes and flavoring additions (e.g., peppermint oil and eucalyptus oil), and sweetening agents, (e.g., saccharin and aspartame).

The pharmaceutical compositions will generally contain from about 0.0001 to 90 wt. %, preferably about 0.01 to 10 wt. % of the active ingredient by weight of the total composition. In addition to the active agent, the pharmaceutical compositions and medicaments can also contain other pharmaceutically active compounds.

Any diluent in the pharmaceutical compositions of the present invention may be any of those mentioned above in relation to the pharmaceutical compositions. Such compositions may include solvents of varying molecular weight as the sole diluent.

The active compound is administered perorally, parenterally (for example, intramuscularly, intraperitoneally, subcutaneously, transdermally or intravenously), rectally or locally, preferably orally or parenterally, especially perlingually, or intravenously.

The dosage rate, e.g., 0.001 to 200 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the infection or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

In addition to the compounds of the present invention, the pharmaceutical composition of this invention may also contain, or be co-administered with, one or more known drugs selected from other clinically useful anti-infective agents. Examples of such anti-infective agents include, for example, amikacin, bacitracin, candicidin, capreomycin, cephalosporins (cefazolin, cephaloglycine, cephaloridine, cephalothin, cephapirin sodium, cephradine), chloramphenicol, colistin (polymyxin), cycloserine, dactinomycin, erythromycin, fusidic acid, gentamicin, gramicidin, kanamycin, lincomycins (clindamycin, lincomycin), neomycin, oleandomycins (oleandomycin, troleandomycin), paromomycin, penicillins (amoxicillin, ampicillin, carbenicillin, carbenicillin, indanyl ester, cloxacillin, dicloxacillin, hetacillin, methacillin, nafcillin, oxacillin, penicillin G (benzylpenicillin), penicillin V (phenoxymetholpenicillin), phenethicillin), rifampin, spectinomycin, staphylomycin, streptomycins (dihydrostreptomycin, streptomycin), tetracyclines (chlortetracycline, demeclocycline, deoxycycline, methacycline, minocycline, oxytetracycline, tetracycline), tyrothricin, vancomycin, and viomycin. Preferred anti-infective agents are those that exhibit augmented or enhanced activity in the presence of the compounds of the present invention, such as erythromycin.

The anti-infective compounds provide action against specific organisms susceptible to them. Examples of microorganisms that the compounds represented by formula (I) are believed to be active against include, but are not limited to alpha-streptococci, beta-streptococci, *Diplococcus pneumoniae,* Staphylococcus species, *Bacillus anthracis, clostridia* spp., *Corynebacterium xerose, Haemophilus ducreyi, Haemophilus influenzae, Escherichia coli,* Klebsiella-Enterococcus species, Neisseria species, *Proteus mirabilis, Salmonella typhosa, Pseudomonas aeruginosa, Histoplasma capsulatum, Coccidioides immitis,* Candida species, *Blastomyces dermatitidis*, Rhondototorula, *Cryptococcus neoformans*, *Sporothrix schenckii*, *Mucor mucedo* and *Aspergillus fumigatus*.

Examples of infections, which may respond to treatment or which may be prevented by administration of the compounds represented by formula (I) include, but are not limited to, skin and soft tissue infections, genitourinary-tract infections, gastrointestinal infections, gonorrhea, respiratory infections, meningitis, aspergillosis, cryptococcosis (torulosis), North American blastomycosis, systemic candidiasis, coccidioidomycosis, histoplasmosis, zygomycosis and subacute bacterial endocarditis.

The appropriate solid or liquid vehicle or diluent may be selected, and the compositions prepared, by methods known to one of ordinary skill in the art. Prevention or treatment of simultaneous infections by more than one bacterium or fungus, or combinations thereof is, of course, contemplated.

The compounds represented by formula (I) may also be employed as antimicrobial agents useful in inhibiting the growth of, including killing, microorganisms present on a surface or in a medium outside a living host. The present invention therefore provides a method for inhibiting the growth of at least one bacterium or fungus present on a surface or in a medium, comprising the step of contacting the surface or medium with one or more compounds represented by formula (I), or a salt thereof, in an amount effective for the inhibition. Thus, the inventive compounds may be employed, for example, as disinfectants for surface treatments, such as disinfection of surgical instruments, or as preservatives for a variety of solid and liquid media susceptible to microbial growth. Suitable amounts of the compounds may be determined by methods known to one of ordinary skill in the art. Compositions comprising at least one compound represented by formula (I), or a salt thereof in an amount effective for inhibiting the growth of at least one bacterium or fungus, and a vehicle or diluent, are also provided by the present invention.

The following examples further illustrate the invention, and are not intended to in any way limit the present claims.

EXAMPLES

1. Synthesis of 3β-Amino-7α,12α-di(1'α-glucosyl)-5β-cholan-24-oic Acid, Methyl Ester 1.1. Preparation of 2,3,4,6-Tetra-O-benzyl-α-D-glucopyranose Methyl-α-D-glucopyranose (100 g, 0.516 mol) is suspended in benzyl chloride (400 mL, 3.5 mol) with KOH pellets (336 g, 6 mol), and the mixture is stirred using a mechanical stirrer at 120°–130° C. for 3 h. The reaction mixture is cooled and water (800 mL) is added to dissolve the crystalline mass, which is extracted with ether (2×200 mL). The combined organic layer is washed with water (2×500 mL) and dried ($Na_2SO_4$). The solvents are removed by vacuum distillation to give the crude methyl 2,3,4,6-tetra-O-benzyl-α-D-glucopyranoside for the next reaction.

To a stirred solution of above crude compound in glacial acetic acid (700 mL) at 110° C. is added 3N sulfuric acid (120 mL) dropwise during 15 min. After 3 h the reaction mixture is cooled to room temperature and left over night for crystallization of product. The crystals are filtered, washed consecutively with water (4×500 mL) and methanol (2×250 mL), and air dried to afford 2,3,4,6-tetra-O-benzyl-α-D-glucopyranose (115 g, 41% overall two steps) as a white powder (mp 150°–51° C., lit. 151°–152° C.; See, Perrine, T. D. et al. *J. Org. Chem.* (1967) 32:664). TLC (EtOAC:Hexane 3:7) $R_f$ 0.2. IR (KBr): 3362, 3030, 2911, 2863, 1454, 1357, 1146, 1088 $cm^{-1}$. $^3$H NMR (300 MHz, $CDCl_3$): δ7.38–7.10 (m, 20H), 5.21 (d, J=3.3 Hz, 1H), 4.98–4.44 (m, 9H), 4.25 (m, 1H) 3.72–3.50 (m, 4H). Anal. Calc. for $C_{34}H_{36}O_6$: C, 75.53; H, 6.71. Found: C, 75.68; H, 6.80.

1.2. Preparation of Phenyl 2,3,4,6-Tetra-O-benzyl-1-thio-D-glucopyranoside

To a stirred solution of 2,3,4,6-tetra-O-benzyl-α-D-glycopyranose (108 g, 0.2 mol) and phenyl disulfide (53 g, 0.24 mol) in dichloromethane (500 mL) is added tri-n-butylphosphine (60 mL, 90%, 0.22 mol). After allowing the reaction mixture to stir at room temperature for 15 h, it is poured into a solution of saturated aqueous sodium bicarbonate (600 mL) and stirred for 10 min. The organic layer is separated, washed with water (2×500 mL), dried ($Na_2SO_4$) and concentrated. The oily residue is dissolved in hexane (500 mL) and chilled to 0° C. to give phenyl 2,3,4,6-tetra-O-benzyl-1-thio-D-glucopyranoside (75 g, 60%) as a white solid (mp 85°–86° C., lit. 84°–85° C. for β-thio compound; See, Ferrier, R. J. et al. *Carbohyd. Res.* (1973) 27:55). TLC (EtOAC:Hexane 1:3) $R_f$ 0.6. IR (KBr): 3061, 3030, 2900, 2865, 1584, 1494, 1453, 1358, 1125, 1085, 1070, 1029 $cm^{-1}$. $^1$H NMR (300 MHz, $CDCl_3$): δ7.70–7.00 (m, 25H), 4.90–4.40 (m, 9H), 3.80–3.40 (m, 6H). Anal. Calc. for $C_{40}H_{40}O_5S$: C, 75.92; H, 6.38, S, 5.06. Found: C, 75.99; H, 6.39; S, 5.12.

1.3. Preparation of Phenyl 2,3,4,6-Tetra-O-benzyl-1-thio-D-glucopyranoside S-Oxide To a stirred cooled (−78° C.) solution of phenyl 2,3,4,5-tetra-O-benzyl-1-thio-D-glucopyranoside (130 g, 0.2 mol) in dichloromethane (400 mL) is added dropwise over a period of 20 min a solution of mCPBA (74%, 58.31 g, 0.25 mol) in dichloromethane (300 mL). The mixture is stirred and allowed to warm up to −30° C. The mixture is then filtered. The filtrate is washed with saturated aqueous sodium bisulfite (2×300 mL), sodium bicarbonate (2×400 mL), brine (400 mL) and water (2×400 mL). The organic layer is dried ($Na_2SO_4$) and concentrated. Flash chromatography ($CH_2Cl_2$:EtOAC 9:1) of the residue furnishes the above-referenced sulfoxide mixture (127 g, 95) as a white solid (mp 120°–122° C.). TLC (EtOH:$CH_2Cl_2$ 1:9) $R_f$ 0.3. IR (KBr): 3060, 3030, 2910, 2867, 1495, 1450, 1360, 1210, 1136, 1092, 1049 $cm^{-1}$. $^1$H NMR ($CDCl_3$): δ7.72–7.14 (m, 25H), 5.12–4.42 (m, 9H), 4.40–3.30 (m, 6H). Anal. Calc. for $C_{40}H_{40}O_6S$: C, 74.04; H, 6.22; S, 4.93. Found: C, 74.10; H, 6.26; S, 4.99.

1.4. Preparation of 3α-p-Methoxybenzoate-5β-cholan-24-oic Acid, Methyl Ester

To a solution of methyl cholate (42.2 g, 0.1 mol), p-anisoyl chloride (20 mL, 0.133 mol) and DMAP (1 g) in pyridine (500 mL) is stirred and refluxed for 8 h. Additional p-anisoyl chloride (10 mL, 0.67 mol) is added and stirred 12 h. The reaction mixture is concentrated, and the residue is dissolved in dichloromethane (600 mL). The solution is washed consecutively with 1N HCl (2×500 mL) and water (3×500 mL), dried ($Na_2SO_4$) and the solvent allowed to evaporate. Crystallization of the residue from EtOAC/hexane (1:1) furnishes the desired acid ester (40 g, 72%) as a white solid (mp 179°–180° C.). TLC (EtOAC:Hexane 7:3) $R_f$ 0.7.

1.5. Preparation of 3α-p-Methoxybenzoate-7α,12α-di(2',3',4',6'-tetra-O-benzyl-1'α-glucosyl)-5β-cholan-24-oic Acid, Methyl Ester Triflic anhydride (30 mL, 0.178 mol) is added to cooled toluene (300 mL, −78° C.) and stirred for 5 min. To this solution, the dried (by azeotropic distillation from toluene) sulfoxide from 1.3 (97 g, 0.1495 mol) dissolved in toluene (300 mL) is added dropwise. After 15 min of stirring, a solution of dried (by azeotropic distillation with toluene) 2,6-di-ter-butyl-4-methyl-pyridine (30.8 g, 0.150 mol) in toluene (100 mL) is added to the reaction mixture and stirred for 10 min at −78° C. To this reaction mixture, dried (by azeotropic distillation with toluene) acid ester from 1.4 (33.36 g, 0.06 mol) in $CH_2Cl_2$ and toluene (1:1, 200 mL) is added dropwise. The reaction progress is monitored by TLC. The temperature of the reaction mixture is slowly brought to $-50°$ C. (during 45 min) and during this time the spot of acid ester from 1.4 on the TLC disappeared completely. The reaction mixture is poured into a saturated aqueous solution of sodium bicarbonate (1000 mL) and stirred for 10 min. The organic layer is separated, and the aqueous layer is extracted with dichloromethane (2×100 mL). The combined organic layers is washed with water (3×500 mL), dried ($Na_2SO_4$) and concentrated. The residue purified by flash chromatography (EtOAC:Hexane=1:9 to 1:4) to furnish the desired bis(glycosylated) acid ester (84 g, 87) as a white foam (mp $46°–48°$ C.). TLC (EtOAC:Hexane 1:3) $R_f$ 0.3. IR (KBr) : 3084, 3062, 3028, 2936, 2867, 1735, 1707, 1605, 1496, 1453, 1360, 1321, 1275, 1254, 1210, 1165, 1097, 1073, 1030 $cm^{-1}$. $^1H$ NMR ($CDCl_3$): $\delta7.60$–6.7 0 (m, 43H), 5.95 (d, 1H, J=9 Hz), 4.99 (d, 1H, J=3.6 Hz), 4.93 (d, 1H, J=6 Hz), 4.88–3.29 (m, 3 1H), 2.68–0.65 (m, 37H) Fab MS: 1624 (M+Na)$^+$. Anal. Calc. for $C_{101}H_{116}O_{17}$: C, 75.71; H, 7.30. Found, C, 75.59; H, 7.31.

1.6. Preparation of 7α,12α-Di(2',3',4',6'-tetra-O-benzyl-1'α-glucosyl)-5β-cholan-24-oic Acid To a stirred solution of the product from is 1.5 (24 g, 15 mmol) in THF (150 mL), NaOH (10 g, 250 mmol) in 95% Ethanol (200 mL) is added and refluxed for 48 h. The reaction mixture is then concentrated, and the residue is dissolved in ethyl acetate (300 mL), washed with water (2×250 mL), saturated aqueous sodium bicarbonate (2×300 mL), brine (300 mL) and dried ($Na_2SO_4$). Solvent is evaporated and the resulting desired compound (18.5 g, 85%) is used for the next step without further purification. TLC (EtOAC:Hexane 1:3) $R_f$ 0.4.

1.7. Preparation of 7α,12α-Di(2',3',4',6'-tetra-O-benzyl-1'α-glucosyl)-5β-cholan-24-oic Acid, Methyl Ester A cooled ($-10°$ C.) solution of diazomethane in ether (100 mL), generated from 5.35 g of diazalid, 25 mmol) is added to a cooled ($-10°$ C.) solution of the product from 1.6 (18.5 g, 12.74 mmol) in ether (100 mL), After 1 h, excess diazomethane is destroyed by adding glacial acetic acid (2 mL) The reaction mixture is washed consecutively with saturated aqueous sodium bicarbonate (2×400 mL), brine (300 mL), and water (300 mL), dried ($Na_2SO_4$) and concentrated. The residue is purified by flash chromatography (EtOAC:Hexane 3:17) to furnish the desired ester (13 g, 70%) as a gum. TLC (EtOAC:Hexane 1:3) $R_f$ 0.6. IR (Neat): 3450, 2925, 2866, 1736, 1453, 1362, 1158, 1071, 1030 $cm^{-1}$. $^1H$ NMR ($CDCl_3$): $\delta7.40$–6.50 (m, 40H), 5.10–3.40 (m, 33H), 2.40–0.71 (m, 38H). Anal. Calc. for $C_{93}H_{110}O_{15}$: C, 76.08; H. 7.56. Found: C, 74.79; H, 7.50.

1.8. Preparation of 3β-Azido-7α,12α-di(2',3',4',6'-tetra-O-benzyl-1'α-glucosyl)-5β-cholan-24-oic Acid, Methyl Ester To a cooled ($0°$ C.) solution of methyl bis(glucosyl) cholate from 1.7 (13 g, 8.87 mmol) and pyridine (2.5 mL, 31 mmol) in dichloromethane (50 mL), triflic anhydride is added and allowed to stir for 20 min. To this mixture, a solution of sodium azide (2.6 g, 40 mmol) in DMF/DMPU (1:1, 250 mL) is then added at $-20°$ C. The reaction mixture is allowed to warm up to room temperature, where it is stirred overnight. The solvents are evaporated, and the residue is dissolved in dichloromethane (200 mL), washed with water (3×200 mL), dried ($Na_2SO_4$), and concentrated. Flash chromatography of the residue on silica (EtOAC:Hexane 3:17) furnished 10 g (75%) of azide compound as a white solid (mp $112°–114°$ C.). TLC (EtOAC:Hexane 1:4) $R_f$ 0.6. IR (KBr):3085, 3061, 3029, 2921, 2867, 2097, 1735, 1603, 1495, 1452, 1360, 1256, 1207, 1160, 1091, 1071, 1031 $cm^{-1}$. $^1H$ NMR ($CDCl_3$): $\delta7.37$–6.84 (m, 40H), 5.15 (d, 1H, J=4 Hz), 4.95 (d, 1H, J=4 Hz), 4.86–4.26 (m, 15H), 4.08–3.40 (m, 16H), 3.62 (s, 3H), 2.60–0.71 (m, 37H), 1.02 (d, 3H), 0.89 (s, 3H) and 0.63 (s, 3H)L Fab MS: 1515 (M+Na)$^+$.

Anal. Calc. for $C_{93}H_{110}O_{14}N_3$: C, 74.76; H, 7.43; N, 2.81. Found: C, 74.84; H, 7.40; N, 2.79.

1.9. Preparation of 3β-Amino-7α,12α-di(2',3',4',6'-tetra-O-benzyl-1'α-glucosyl)-5β-cholan-24-oic Acid, Methyl Ester A solution of compound azide of 1.8 (11 g, 7.38 mmol) and $Ph_3P$ (5.76 g, 22 mmol) in 90% aqueous THF (100 mL) is stirred and refluxed for 48 h. The reaction mixture is concentrated, and the residue is purified by flash chromatograph ($CH_2Cl_2$ and then $CH_2Cl_2$:EtOH=98:2 to 9:1) to give the desired 3-amino compound (6 g, 56%) as a white solid (mp $43°–45°$ C.). TLC (EtOH:$CH_2Cl_2$ 1:19) $R_f$ 0.15. IR (KBr): 3418, 2922, 2868, 1736, 1496, 1453, 1362, 1161, 1071, 1032 $cm^{-1}$. $^1H$ NMR ($CDCl_3$): $\delta7.38$–6.84 (m, 40H), 5.10–3.48 (m, 33H), 2.62–0.70 (m, 37H). Anal. Calc. for $C_{93}H_{112}O_{14}N$: C, 76.08; H, 7.70; N, 0.95. Found: C, 75.82; H, 7.71; N, 0.89.

1.10. Preparation of 3β-Amino-7α,12α-di(1'α-glucosyl)-5β-cholan-24-oic Acid, Methyl Ester To a solution of the 3-amino compound of 1.9 (14.65 g, 10 mmol) in toluene (50 mL) and ethanol (200 mL) is added formic acid (15 mL) and palladium hydroxide (20%) on carbon (15 g). The resulting mixture is stirred for 24 h under a hydrogen atmosphere at 40 psi. TLC indicated incomplete hydrogenolysis. Additional formic acid (4 mL) and catalyst (4 g) is then added, and the hydrogenation reaction allowed to proceed for another 24 h. The reaction mixture is then filtered through sand over a membrane filter and concentrated. The filtrate is then mixed with ethyl acetate to form a precipitate. (In some instances, the methanol solvent from the hydrogenation reaction may need to be removed.) The filtered precipitate is then dissolved in 25 mL deionized water and freeze-dried. Flash Chromatography gave 2.82 g (38%) of the deprotected amino cholate ester as white foam (mp $170°–172°$ C., decomp.). TLC (MeOH:$CH_2Cl_2$:Isopropylamine 2:2:1) $R_f$ 0.15. IR (KBr): 3450, 2932, 1736, 1595, 1451, 1381, 1151, 1023 $cm^{-1}$. $^1H$ NMR ($CDCl_3$) : $\delta5.05$ (d, 1H), 4.80 (d, 1H), 3.91–3.10 (m, 15H), 2.50–0.58 (m, 37H). MS (Fab) : 746 (M+H)$^+$. Anal. Calc. for $C_{37}H_{63}O_{14}N$: C, 59.56; H, 8.52; N, 1.88. Found: C, 54.60; H, 8.47; N, 2.49.

The corresponding 3α-amino compound can be obtained from the 3β-hydroxy starting material similarly. The 3β-hydroxy starting material can be obtained, for example, by treatment of methyl cholate with diethyl azidodicarboxylate in the presence of formic acid and triphenyl phosphine with inversion of stereochemistry to provide the methyl 30β-O-formylcholate, which, subsequently, can be hydrolyzed or manipulated, as needed.

2. Preparation of 3α-p-Methoxybenzoate-7α,12α-di(1'α-glucosyl)-5β-cholan-24-oic Acid, Methyl Ester To a solution of the acid ester of 1.5 (10 mmol; see, above) in toluene (50 mL) and ethanol (200 mL) is added formic acid (15 mL) and palladium hydroxide (20%) on carbon (15 g). The resulting mixture is stirred for 24 h under a hydrogen atmosphere at 40 psi. (Additional formic acid and catalyst can be added, if desired, if TLC analysis reveals that the reaction is incomplete after the initial 24 h reaction period. A second 24 h reaction period can then be initiated.) The reaction mixture is then filtered through sand over a membrane filter and concentrated. The filtrate is then mixed with ethyl acetate to form a precipitate. (Some of the methanol solvent from the hydrogenation reaction may need to be removed.) The filtered precipitate is then dissolved in 25 mL deionized water and freeze-dried. Subjecting the residue to flash column chromatography gave the title compound in ca. 38% yield.

$^1$H NMR (CD$_3$OD) : δ0.71 (s, 3H, 18-H), 0.90 (d, 3H, 21-H, J=6.6 Hz), 0.93 (s, 3H, 19-H), 1.0–2.6 (m), 3.2–3.4 (m, 2H), 3.55 (s, 3H, CO$_2$CH$_3$), 3.65 (m), 3.76 (s, 3H, anisoyl-4-methyl), 4.83 (d, 1H, anomeric H), 5.02 (d, 1H, anomeric H), 6.87 (d, 2H, anisoyl aromatic, J=9 Hz), 7.92 (d, 2H, anisoyl aromatic, J=9 Hz).

3. Synthesis of the Activated Ester of Deoxycholate

Triethylamine (10 mL, 71.2 mmol) is added to a stirred solution of the sodium salt of deoxycholic acid (15 g, 34.7 mmol), N-hydroxysuccinimide (7.5 g, 65.2 mmol) and 1-(3-dimethylaminopropyl)-3-ethylcarbodiimide (13.2 g, 69.3 mmol, EDC) in dichloromethane. The mixture is stirred for 12 h. The reaction mixture is then diluted with water (150 mL) and extracted twice with dichloromethane. The organic layers are combined, dried over MgSO$_4$, filtered, and concentrated under reduced pressure to provide a solid residue. The residue is recrystallized from ethyl acetate-petroleum ether to give 5.5 g (30%) of product. Selected $^1$H resonances: (270 MHz, CDCl$_3$): δ4.00 (br s, 1H, C12), 3.6 (m, 1H, C3), 1.03 (d, 3H, C21), 0.9 and 0.68 (s, 3H each, angular methyls of steroid).

4. Synthesis of the Deoxycholic Acid-Spermine Conjugate (Comp. A of Table 1)

Spermine (0.3 g, 1.18 mmol) is added to a stirred solution of the activated ester of deoxycholate from Example 3 (0.15 g, 0.28 mmol) and triethylamine (0.1 mL, 0.71 mmol) in dichloromethane. The mixture is stirred for 0.5 h and a precipitate is observed. The solids are filtered through a buchner funnel. The filtrate is washed with water (10 mL). The organic layer is concentrated to give a residue (0.18 g). The residue is acidified with methanolic trifluoroacetic acid. The resulting solution is purified by reverse phase chromatography to give 0.14 g (80%) of the steroid-polyamine conjugate. Selected $^1$H resonances: (270 MHz, CD$_3$OD): δ3.98 (br s, 1H, C12), 3.55 (m, 1H, C3), 3.4 (br t, 2H, spermine methylenes next to amide linkage), 3.0 (br s, 10H, spermine methylenes except those next to amide), 1.03 (d, 3H, C21), 0.9 and 0.68 (s, 3H each, angular methyls of steroid). High resolution mass spectrometry confirmed the proper molecular weight.

In the same fashion, other non-glycosylated amphiphatic steroidal compounds, including but not limited to cholic acid or chenodeoxycholic acid, may be conjugated to a polyamine molecule, including but not limited to ethylene diamine, diethylene triamine, spermidine, other polyalkylenepolyamines, and the like.

5. Synthesis of 3α-Hydroxy-7α,12α-di(1'α-glycosyl)-5β-cholan-24-oic Acid

Figure 6:
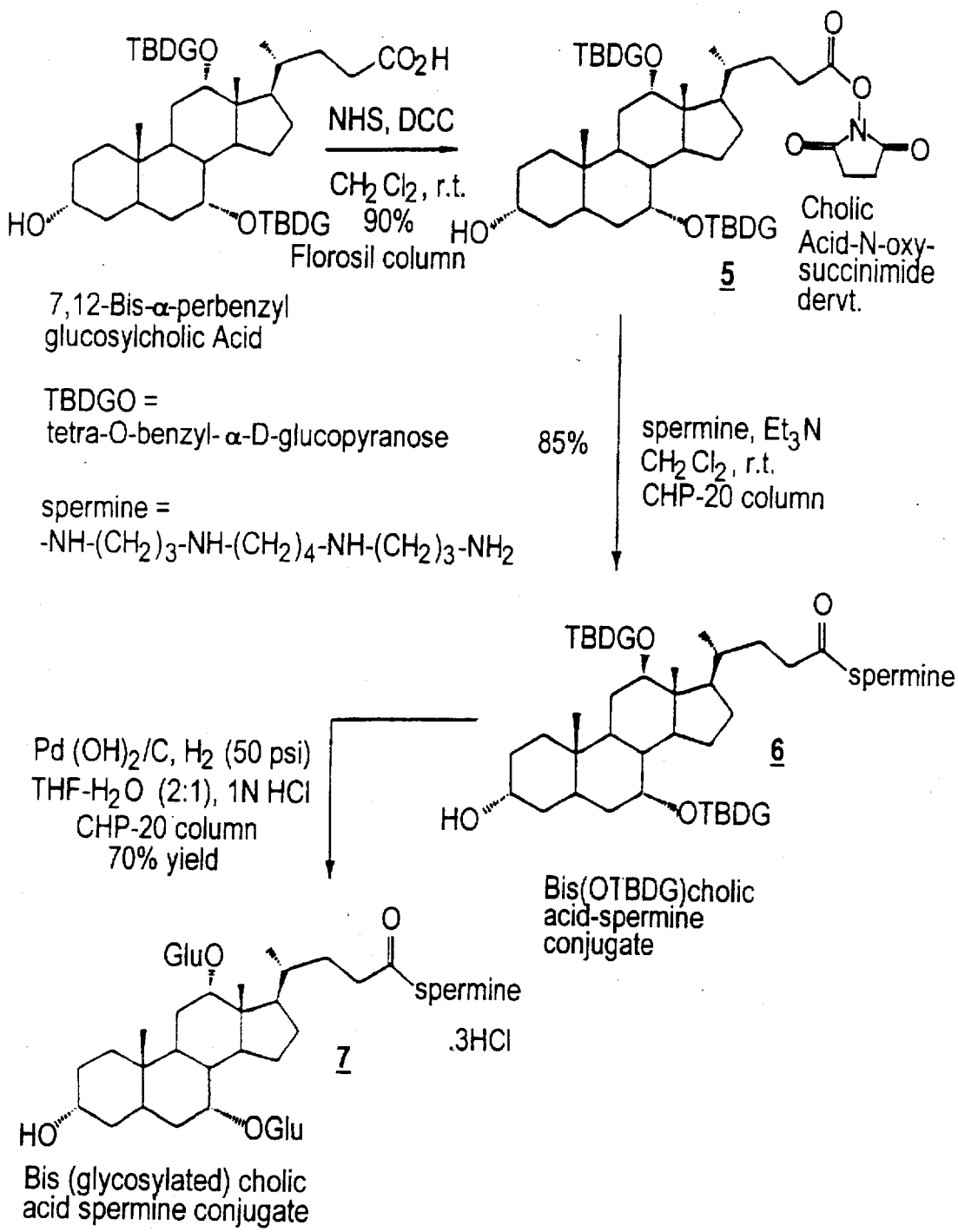
FIG. 6 illustrates the synthetic scheme for the preparation of 3α-hydroxy-7α,12α-di(1'α-glucosyl)-5β-cholan-24-oic acid, N-(4,9-diaza-12-aminododecyl)amide (may also be referred to as the bis(glycosylated)cholic acid-spermine conjugate, Compound C).
Figure 7:
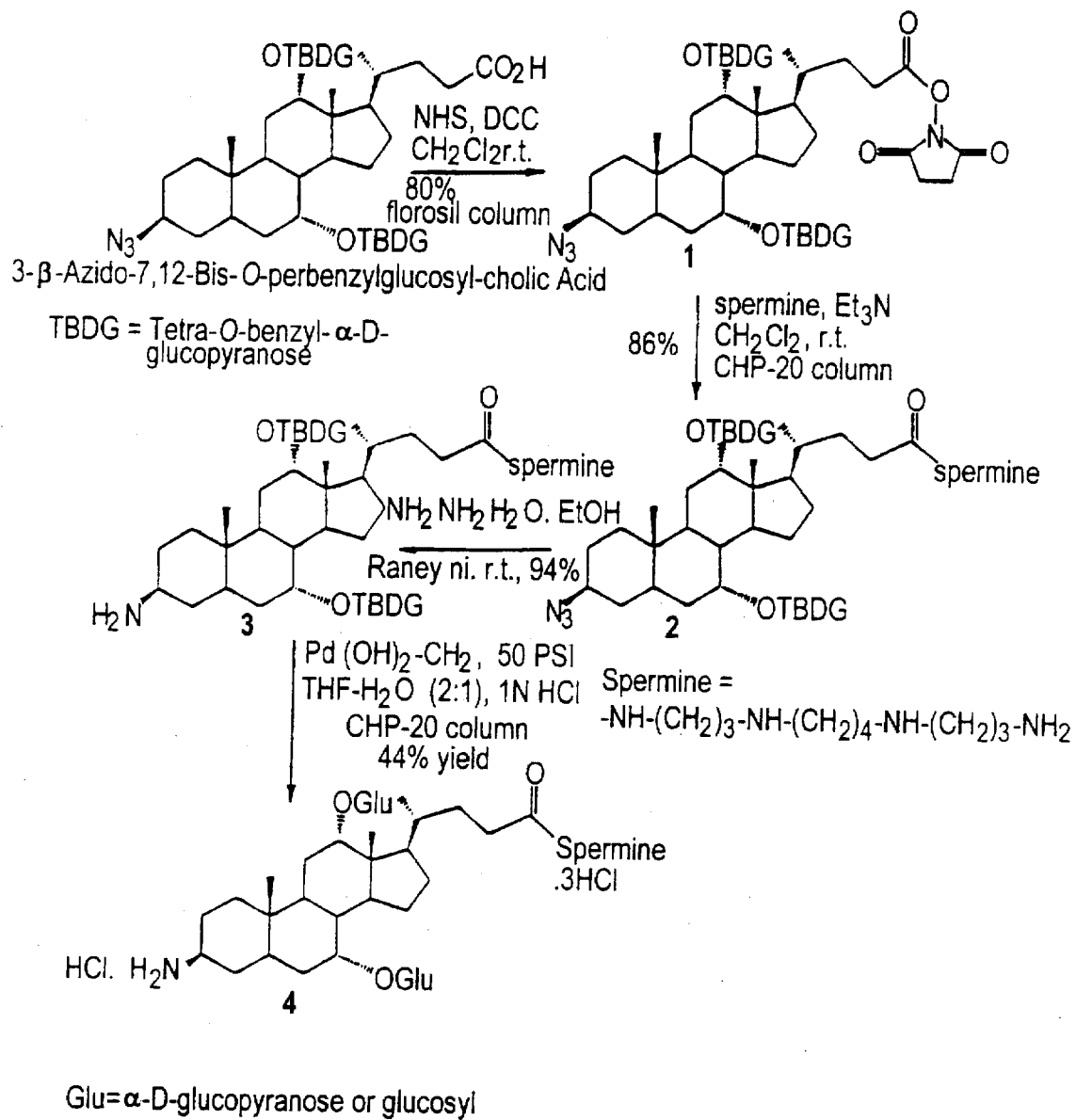
FIG. 7 illustrates the synthetic scheme for the preparation of 3β-amino-7α,12α-di(1'α-glucosyl)-5β-cholan-24-oic acid, N-(4,9-diaza-12-aminododecyl)amide trihydrochloride.
Figure 8B:
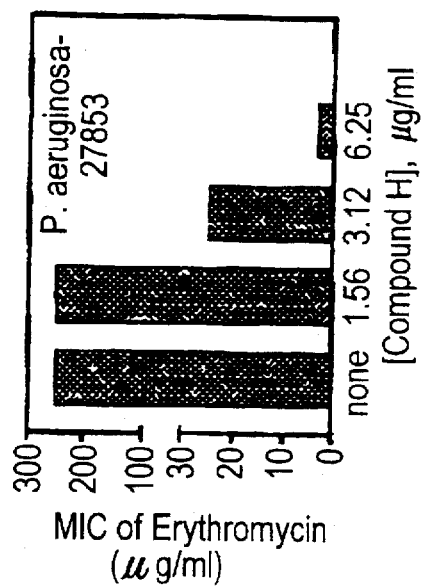
FIG. 8A and 8B show the effects of compound H on the MIC of Erythromycin for *E. coli* 25922 and *P. aeruginosa* 27853.
Figure 8A:
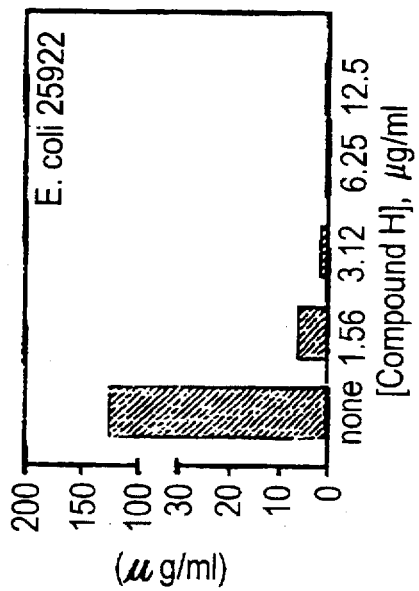
Figure 9B:
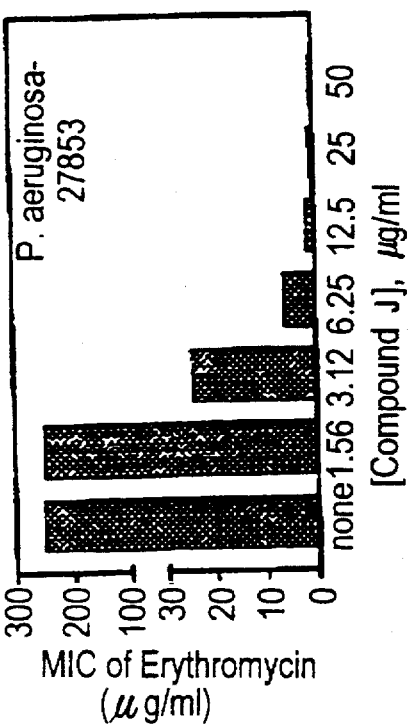
FIG. 9A and 9B show the effects of compound J on the MIC of Erythromycin for *E. coli* 25922 and *P. aeruginosa* 27853.
Figure 9A:
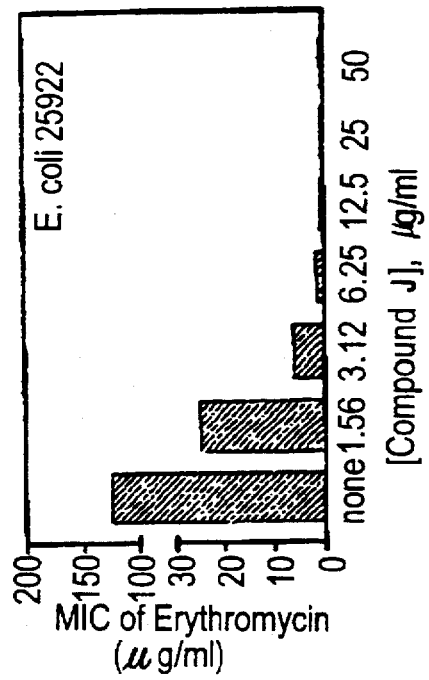
Figure 10B:
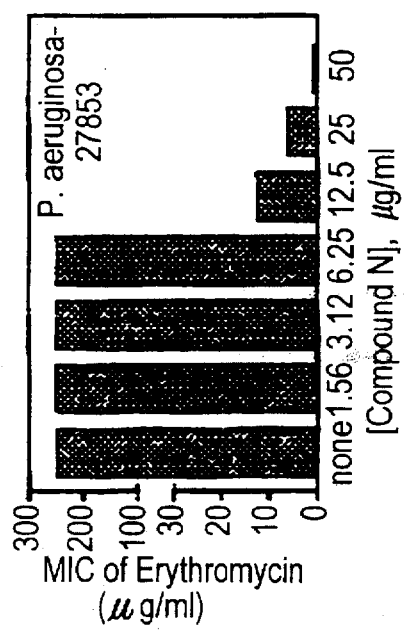
FIG. 10A and 10B show the effects of compound N on the MIC of Erythromycin for *E. coli* 25922 and *P. aeruginosa* 27853.
Figure 10A:
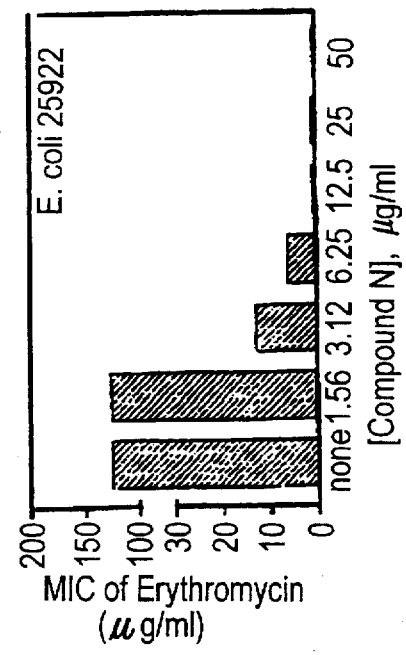

To a stirred solution of the methylcholate product of Example 2, above, (15 mmol) in THF (150 mL) is added NaOH (10 g, 250 mmol) in 95% ethanol (200 mL). The reaction mixture is refluxed for 48 h. The reaction mixture is then concentrated, acidified with dilute Hcl and the residue is dissolved in ethyl acetate (300 mL), washed with water (2×250 mL), saturated aqueous sodium bicarbonate (2×300 mL), brine (300 mL) and dried (Na$_2$SO$_4$). Solvent is evaporated to provide the 7,12-bis-α-perbenzylglucosylcholic acid product in 80% yield. (See, FIG. 6.) Activation of the carboxylic acid group is carried out as follows.

6. Synthesis of the Bis(glycosylated)cholic Acid-Spermine Conjugate (Comp. C of Table 1) via the Activated Acid Triethylamine (120 µL, 0.8 mmol) is added to a stirred solution of the cholic acid product of Example 5 (0.3 g, 0.2 mmol), N-hydroxysuccinimide (72 mg, 0.6 mmol) and 1-(3-dimethylaminopropyl)-3-ethylcarbodiimide (160 mg, 0.8 mmol) in dichloromethane. The mixture is stirred for 12 h. After this time, the reaction mixture is diluted with water (50 mL) and extracted twice with dichloromethane. The organic layers are combined, dried over MgSO$_4$, filtered, and concentrated under reduced pressure to provide a solid residue 0.33 g (96%) of the activated ester. (See, Comp. 5 of FIG. 6.)

To a stirred solution of the activated ester (0.15 g, 0.089 mmol) and triethylamine (50 mL, 0.35 mmol) in dichloromethane is added spermine (0.3 g, 0.61 mmol). The mixture is stirred for 0.5 h and a precipitate is observed. The solids are filtered over a buchner funnel. The filtrate is washed with water (10 mL). The organic layer is concentrated to give a residue (0.18 g). The residue is acidified with methanolic trifluoroacetic acid. The resulting solution is purified by reverse phase chromatography to give 0.14 g (85%) of the protected bis(glycosylated)cholic acid-spermine conjugate.

In the same fashion, other glycosylated amphiphatic steroidal compounds, including but not limited to the mono-, di-, or triglycosylated forms (as appropriate) of cholic acid, 7-deoxycholic acid, or chenodeoxycholic acid, may be conjugated to a polyamine molecule, including but not limited to ethylene diamine, diethylene triamine, spermine, spermidine, other polyalkylenepolyamines, and the like.

7 Deprotection o f the Protected Bis(glycosylated) cholic Acid-Spermine Conjugate A hydrogenation flask is charged with a solution of the protected bis(glycosylated)cholic acid-spermine conjugate (0.11 g, 0.06 mmol; see, above) in a mixture of methanol (20 mL) and benzene (4 mL) or THF, followed by Pd(OH)$_2$ catalyst and formic acid (1 mL) or hydrochloric acid. The reaction mixture is shaken under a hydrogen atmosphere at 50 psi for 40 h. The catalyst is filtered off with Celite®, and the solvent is removed by evaporation under reduced pressure. The product is purified over Sephadex-LH-20 gel, eluting with MeOH, to give the desired bisglycosteroid-spermine conjugate (Comp. C).

Figure 3:
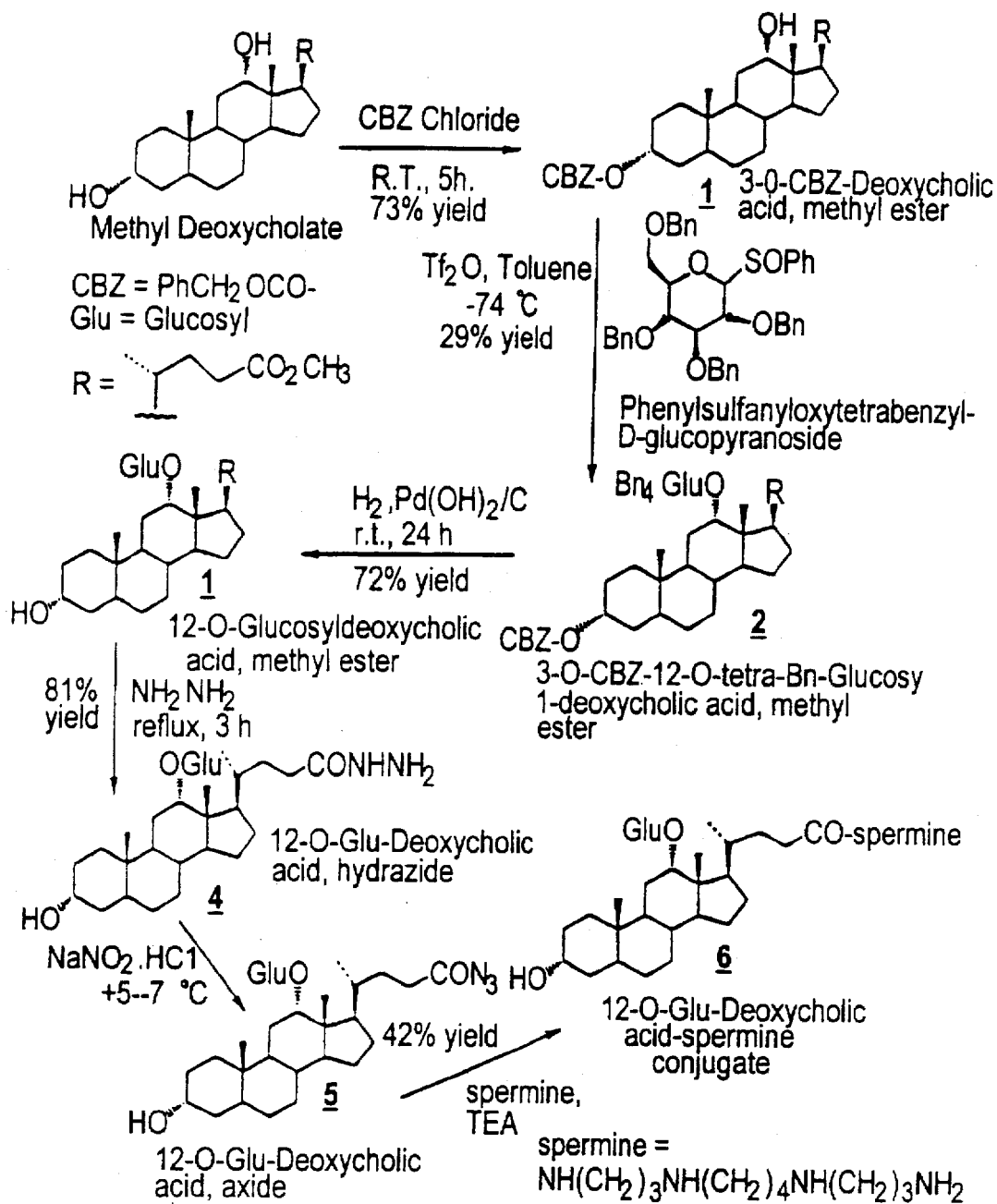
FIG. 3 illustrates the synthetic scheme for the preparation of 3α-hydroxy-7-deoxy-12α-(1'α-glucosyl)-5β-cholan-24-oic acid, N-(4,9-diaza-12-aminododecyl)amide (may also be referred to as the 12-(glycosylated)deoxycholic acid-spermine conjugate, Compound D)

8. Synthesis of the 12α-(O-Glucosyl)deoxycholic Acid-Spermine Conjugate (Comp. D of Table 1 and Comp. 6 of FIG. 3)

8.1. Preparation of 3α-O-CBZ-Deoxycholic Acid, Methyl Ester (Comp. 1 of FIG. 3)

A mixture of methyldeoxycholate (25 g, 61 mmol), benzylchloroformate (17.0 g, 14 mL, 100 mmol), dimethylaminopyridine (1.22 g, 10 mmol), pyridine (30 mL) and dioxane (150 mL) are stirred at room temperature 3 h, the additional amounts of the benzylchloroformate (12.0 g, 10 mL) are added two times in 2 h to complete reaction. Total amount of the benzylchloroformate is 41.0 g (34 mL). The reaction mixture is poured into a separatory funnel, water (500 mL) and ethyl acetate (300 mL) are added. The organic layer is washed with water (500 mL×2), dried over sodium sulfate, concentrated to give an oil. The product is purified on flash chromatography over silica gel (EA-Hexane 1:1) providing 24.0 g (73% yield) of comp. 1 as a thick oil. TLC (EA:Hexane 2:5) R$_f$ 0.65. IR (neat):3553 (OH), 2943, 2869 (CH), 1742 (C═O), 1453, 1389, 1263 (arom.), 944, 911, 789, 747, 696 cm$^{-1}$. $^1$H NMR (CDCl$_3$): δ7.38 (s, 5H) 5.15 (s, 2H), 3.6 (s, 3H), 2.0–1.0 (m, 24H), 0.96 (d,3H, J=6 Hz), 0.86 (s, 3H), 0.65 (s, 3H).

8.2. Preparation of 3α-O-CBZ-12α-(Tetra-O-benzyl-O-glucosyl)deoxycholic Acid, Methyl Ester (Comp. 2 of FIG. 3)

Triflic anhydride (2.08 g, 1.26 mL, 7.4 mmol) is added to dry toluene (100 mL), chilled to −75° C. with acetone-dry ice bath, then phenylsulphenyl tetra-O-benzylglucopyranoside (glucosulfoxide) (5.06 g, 7.4 mmol) is added dropwise, and in 10 minutes the 2,6-tert-butyl-4-methyl-pyridine, and then 3-O-CBZ-Deoxymethyl cholate 1 is added dropwise. When TLC showed the reaction is finished, it is quenched by sodium bicarbonate (saturated solution, 200 mL) at −25° to −30° C. The organic layer is dried over sodium sulfate, concentrated in vacuum at +50° to +60° C. The residue on flash chromatography (EA-Hexane, 20% of EA) afforded 2 (1.8 g, 296), as thick colorless oil. TLC (EA-Hexane 2:5) $R_f$ 0.70. $^1$H NMR (CDCl$_3$): δ7.3 (m, 24H), 4.4–5.0 (m, 10H), 3.6 (s, 3H), 3.4–4.0 (m, 7H), 1.0–1.95 (m, 40H), 0.92 (d, 3H), 0.82 (s, 3H), 0.56 (s, 3H).

8.3. Preparation of 12α-(O-Glucosyl)deoxycholic Acid, Methyl Ester (Comp. 3 of FIG. 3)

The comp. 2 (1.6 g, 1.47 mmol) is dissolved in ethyl acetate (15 mL) and ethanol (50 mL) together with catalyst Pd(OH)$_2$/C (500 mg). Using a Parr shaker, the reaction mixture is pressurized under hydrogen at 50 psi for 24 h. The catalyst is filtered off, and the filtrate is evaporated to give a crystalline residue. The residue is purified by flash chromatography (EtOH-DCM 2:8) to afford comp. 3 (0.65 g, yield 72%) as white crystals, m.p. 186°–188° C. TLC (EtOH-DCM 2:8) $R_f$ 0.5. IR (neat): 3510, 2943, 2585, 1690, 1452, 1376, 1148, 1090, 1050 cm$^{-1}$. $^1$H NMR: δ5.05 (d, 1H, J=3 Hz), 3.9 (s, 1H), 3.7–3.8 (m, 3H), 3.6 (s, 3H), 2.2–1.4 (m, 40H), 0.95 (d, 3H), 0.90 (s, 3H), 0.72 (s, 3H).

8.4. Preparation of 12α-(O-Glucosyl)deoxycholic Acid, Hydrazide (Comp. 4 of FIG. 3)

The methyl ester 3 (0.6 g, 1.1 mmol) is refluxed in 5 mL of EtOH-hydrazine hydrate (10:1) for 3 h. The solvent is evaporated, water (50 mL) added, then distilled off to remove excess of hydrazine hydrate. The residue is azeotroped with toluene to afford a colorless crystalline hydrazide 4 (0.50 g, yield 81%, m.p. 180°–182° C.). TLC (EtOH-DCM 2:5) $R_f$ 0.15. Anal. Calc. for C$_{30}$H$_{52}$N$_2$O$_8$: N 5.0. Found: N 4.81. IR (KBr) 3393, 2907, 2863, 1633, 1543, 1452, 1372, 1144, 1016, 704 cm$^{-1}$.

8.5. Preparation of 12α-(O-Glucosyl)deoxycholic Acid, Azide (Comp. 5 of FIG. 3)

Hydrazide 4 (0.5 g, 0.88 mmol) is dissolved in 5 mL of 10% HCl at +1° to +3° C. to give a clear solution. Then NaNO$_2$ (0.14 g, 2.0 mmol) in 5 mL of water is added dropwise at +1° to +5° C. to the reaction mixture to afford a precipitate of the azide 5. This azide is unstable and could not be isolated in pure form. IR (KBr): 3485–3290, 2928, 2866, 2270, and 2134 (CON$_3$), 1690, 1651, 1451, 1376, 1147, 1031 cm$^{-1}$. TLC (EtOH-DCM 2:5) $R_f$ 0.35.

8.6. Preparation of 12α-(O-Glucosyl)deoxycholic Acid-Spermine Conjugate (Comp. D)

The precipitate of azide 5 is fast filtered off through a glass filter with porosity 40–60 μm and washed with ice water (10 mL). While still wet, the precipitate of azide 5 is immediately transferred into a solution of spermine (0.5 g, 2.5 mmol) and triethylamine (0.5 mL) in 10 mL of water. The resulting mixture is stirred for 30 min, then heated up to 60° C. for 10 min, chilled to room temperature, and treated with acetic acid to a pH 4.5–5.0. The clear solution of spermine derivative D is purified by flash chromatography using a reverse-phase column CHP 20 in MeOH-Water. The spermine derivative D is eluted with a solvent gradient ranging from 50–100% of MeOH. The water-methanol fractions are combined and concentrated. The pH is adjusted to 3.5–3.0 with HCl. The clear solution is lyophilized to afford white, highly hygroscopic, crystalline spermine derivative D (0.37 g, yield 42% based on hydrazide 4, 180° C. sinks, 200° C. decomposition). TLC (MeOH-DCM 2:8) $R_f$ 0.1; (MeOH-isopropylamine-DCM 2:2:6) $R_f$ 0.55. IR (KBr): 3450, 2943, 1690, 1452, 1376, 1148, 1091, 950 cm$^{-1}$. $^1$H NMR (D$_2$O): δ4.95 (d, 1H, J=3 Hz), 3.9 (s, 1H), 3.65 (m, 3H), 3.4 (m, 3H), 3.0 (m, 3H), 1.0–2.4 (m, 60H), 0.95 (d, 3H), 0.90 (s, 3H), 0.62 (s, 3H). Anal. Calc. for C$_{40}$H$_{74}$N$_4$O$_8$·3HCl·10H$_2$O: C 46.7, H 8.91, N 5.45, Cl 10.2. Found: C 56.02, H 8.91, N 5.66, C 9.47. F.W. 739.5. Found: M+Na$^+$ =763.

Figure 4:
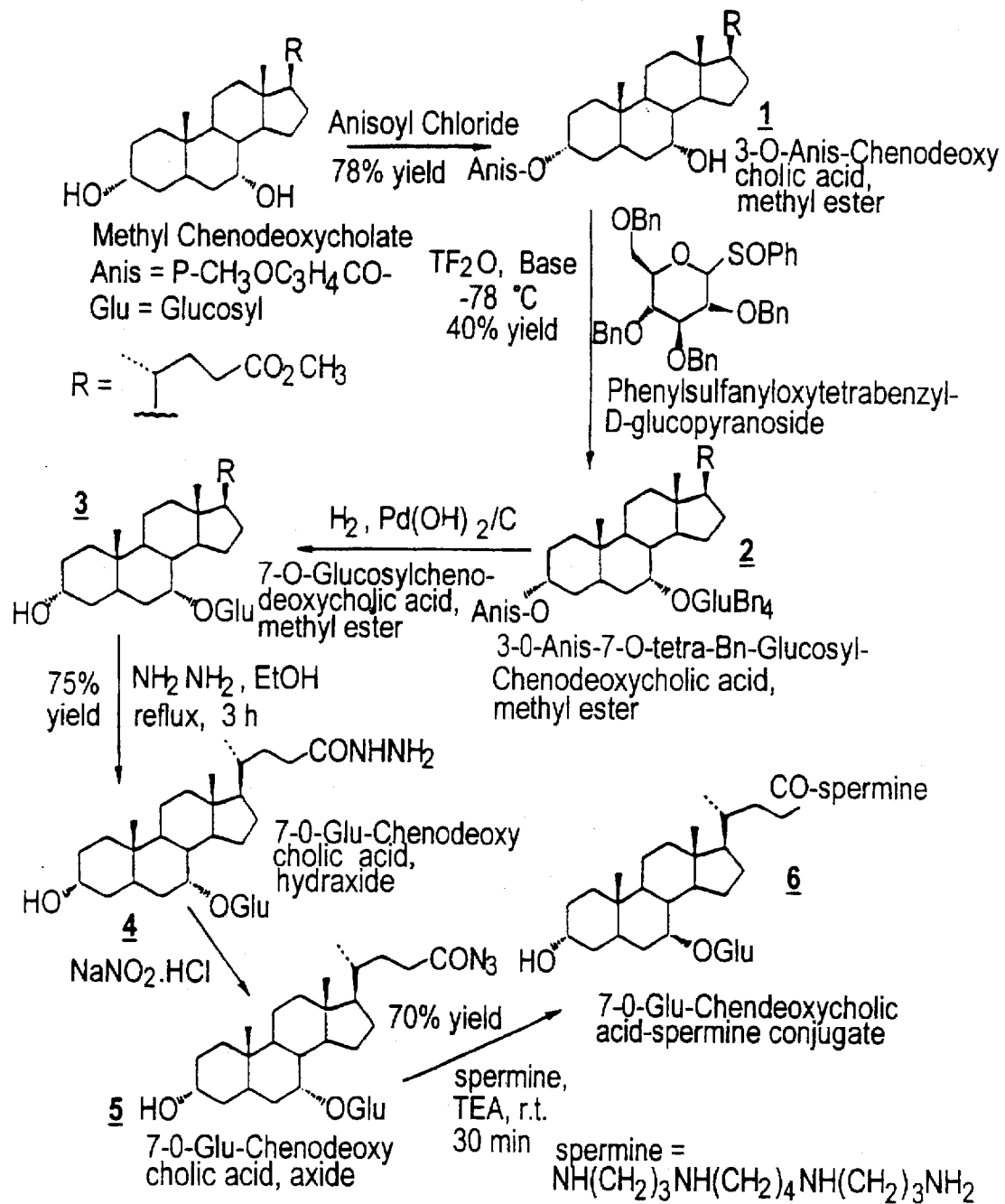
FIG. 4 illustrates the synthetic scheme for the preparation of 3α-hydroxy-12-deoxy-7α-(1'α-glucosyl)-5β-cholan-24-oic acid, N-(4,9-diaza-12-aminododecyl)amide (may also be referred to as the 7-(glycosylated)chenodeoxycholic acid-spermine conjugate, Compound E)

9. Synthesis of the 7α-(O-Glucosyl)chenodeoxycholic Acid-Spermine Conjugate (Comp. E of Table 1 or Comp. 6 of FIG. 4)

9.1. Preparation of 3α-(O-Anisoyl)chenodeoxycholic Acid, Methyl Ester (Comp. 1 of FIG. 4)

A mixture of methyl chenodeoxycholate (5.0 g, 12.3 mmol), anisoyl chloride (2.3 g, 2.0 mL, 13.5 mmol), dimethylaminopyridine (0.8 g, 6.5 mmol) in pyridine (15 mL) is heated at 100° C. for 3 h. Reaction mixture is poured into a separatory funnel, water (200 mL) and ethyl acetate (300 mL) is added. The organic layer is washed with 5% HCl (100 mL), water (200 mL), sodium bicarbonate, and dried over sodium sulfate. Sometimes a precipitate of the product appeared between layers. This precipitate may be filtered off and combined with the product that is obtained after evaporation of ethyl acetate. Total amount is 5.2 g (yield 78%, m.p. 188°–190° C. from EtOH). TLC (EA-Hexane 2:5) $R_f$ 0.6. IR (KBr): 3513 (OH), 2938, 2851, 1730 (COOCH$_3$), 1712 (Anis-CO), 1607, 1579, 1509, 1451, 1279, 1165, 1100, 963, 770 cm$^{-1}$. $^1$H NMR (CDCl$_3$): δ8.03 (d, 2H), 7.96 (d, 2H), 4.85 (s, 1H), 3.85 (s, 3H), 3.65 (s, 3H), 2.0–1.0 (m, 24H), 0.96 (d, 3H), 0.90 (s, 3H), 0.66 (s, 3H).

9.2. Preparation of 3α-(O-Anisoyl)-7a-(tetra-O-benzyl-O-glucosyl)chenodeoxycholic Acid, Methyl Ester (Comp. 2 of FIG. 4)

Triflic anhydride (2.1 g, 1.27 mL, 7.4 mmol) is added to dry toluene (100 mL), chilled up to −72° to −75° C. with acetone-dry ice bath. Phenylsulphenyl glucoside (5.1 g, 7.4 mmol) in 20 mL of dry toluene is added dropwise, then in 10 mins the 2,6-di-tert-butyl-4-methyl-pyridine (1.52 g, 7.4 mmol) in toluene (15 mL) is added, and in 5 min the anisoyl derivate 1 (3.2 g, 5.9 mmol in 30 mL of dry toluene) is added dropwise. When TLC showed the starting material disappeared, saturated solution of the sodium bicarbonate (150 mL) is poured, and the mixture is transferred into a separatory funnel. The organic layer is washed with water (20 mL), brine (50 mL), dried over sodium sulfate, and concentrated to give a thick oil. It is purified by flash chromatography (EA-Hexane); the product is eluted with 20% ethyl acetate. The product (4.0 g, yield 62%) is obtained as a thick colorless oil. TLC (EA-Hexane 2:5) $R_f$ 0.65. IR (neat): 2950, 2870, 1690, 1745, 1610, 1450, 1275, 1160, 1050, 970, 775 cm$^{-1}$.

9.3. Preparation of 3α-(Anisoyl)-7α-(O-glucosyl) chenodeoxycholic Acid, Methyl Ester (Comp. 3 of FIG. 4)

The above obtained oil (4.0 g, 3.7 mmol) is dissolved in ethyl acetate (15 mL) and ethanol (75 mL), together with catalyst (Pd(OH)$_2$/C, 2.0 g). Formic acid (2.0 mL) is added to the mixture. The mixture is set up for hydrogenation in an 0.5 L Parr's apparatus at 50 psi for 24 h. The catalyst is filtered off, and the filtrate is evaporated to give a crystalline residue of 3 (1.8 g, yield 69%), m.p. 258°–2600° C. (from EtOH), no decomposition. TLC (MeOH-DCM 1:9) $R_f$ 0.35. IR (KBr): 3439 (OH), 2863, 1742 (COOCH$_3$), 1684 (anis. CO), 1606, 1284, 1260, 1022, 967, 773 cm$^{-1}$. $^1$H NMR (CDCl$_3$): δ7.9 (d, 2H, J=6 Hz), 6.8 (d, 2H, J=6 Hz), 4.95 (d, 1H, J=3 Hz), 4.75 (s, 1H), 3.80 (s, 3H), 3.58 (s, 3H), 3.3–3.5 (m, 4H), 2.0–1.1 (m, 30H), 0.92 (s, 3H), 0.88 (d, 3H) 0.62 (s, 3H).

9.4. Preparation of 7α-(O-Glucosyl) chenodeoxycholic Acid, Hydrazide (Comp. 4 of FIG. 4)

The methyl ester 3 (1.7 g, 3.0 mmol) is refluxed in mixture EtOH-hydrazide hydrate (20 mL+6 mL) for 2 h. The crystals of hydrazide 4 (0.45 g, m.p. 238°–240° C.) that form are separated from solution at room temperature and filtered off. The mother liquid is concentrated, to afford an additional amount of hydrazide 4 (0.65 g). Total yield 1.1 g (70%). TLC (MeOH-DCM, 2:8) $R_f$ 0.05. IR(KBr): 3378 (NH, OH), 2927, 1697 (CONH), 1601, 1260, 1020, 980, 770 cm$^{-1}$.

9.5. Preparation of 7α-(O-Glucosyl)Chenodeoxycholic Acid, Azide (Comp. 5 of FIG. 4)

Hydrazide 4 (0.8 g, 1.4 mmol) is dissolved in 10 mL 10% HCl, chilled to +3° to +5° C., then $NaNO_2$ (0.21 g, 3 mmol) in 5.0 mL of water is added dropwise affording a precipitate of azide 5. This compound is unstable and cannot be isolated as a pure substance. TLC (EtOH-DCM 2:8) $R_f$ 0.45. IR (KBr) : 3490–3300, 2930, 2850, 2260 and 2133 ($CON_3$), 1700, 1640, 1450, 1366, 1147, 1050 cm$^{-1}$.

9.6. Preparation of 7α-(O-Glucosyl)chenodeoxycholic Acid-Spermine Conjugate (Comp. E)

The precipitate of azide 5 is fast filtered through a glass filter (porosity 40–60 µm), washed with ice water (5 mL), and while wet is immediately transferred into a solution of spermine (0.5 g, 2.5 mmol) and triethylamine (0.5 mL) in 10 mL of water. The mixture is stirred for 30 min, then is heated up to 60° C. for 10 min, then is chilled to room temperature. The pH is adjusted to 4.5–5.0 using acetic acid. The insoluble impurities are filtered off, and the clear filtrate of spermide E is purified by flash chromatography using a reverse-phase column CHP-20. The spermide E is eluted with a solvent gradient ranging from 40–100% of MeOH. The water-methanol fractions are combined, evaporated to dryness. Water (10 mL) and concentrated HCl (0.2 mL) is added, and the clear solution is lyophilized to afford white, highly hygroscopic, crystalline spermide E (0.50 g, yield 42% based on hydrazide 4, m.p. 162°–164° C. with decomp.). TLC (MeOH-i-PrOH-DCM 2:2:6) $R_f$ 0.6. IR (KBr): 3447, 2934, 2865, 1652 (CONH), 1457, 1379, 1256, 1026, 772 cm$^{-1}$. $^1$H NMR ($D_2O$): δ4.85 (d, 1H, J=3 Hz), 3.5–3.8 (m, 8H), 3.5 (m, 6H), 3.1 (m, 2H), 2.9–3.0 (m, 10H), 2.1–1.0 (m, 40H), 0.796 (m, 6H), 0.551 (s, 3H) Anal. Calc. for $C_{40}H_{74}N_4O_8 \cdot 3HCl \cdot 10H_2O$: C 46.7, H 9.44, N 5.45, Cl 10.37. Found: C 60.8, H 8.97, N 4.60, Cl 6.09. F.W. 847.5. Mass-spectrum Fab.M–HCl+H$^+$=815. Found: 815.

Figure 5:
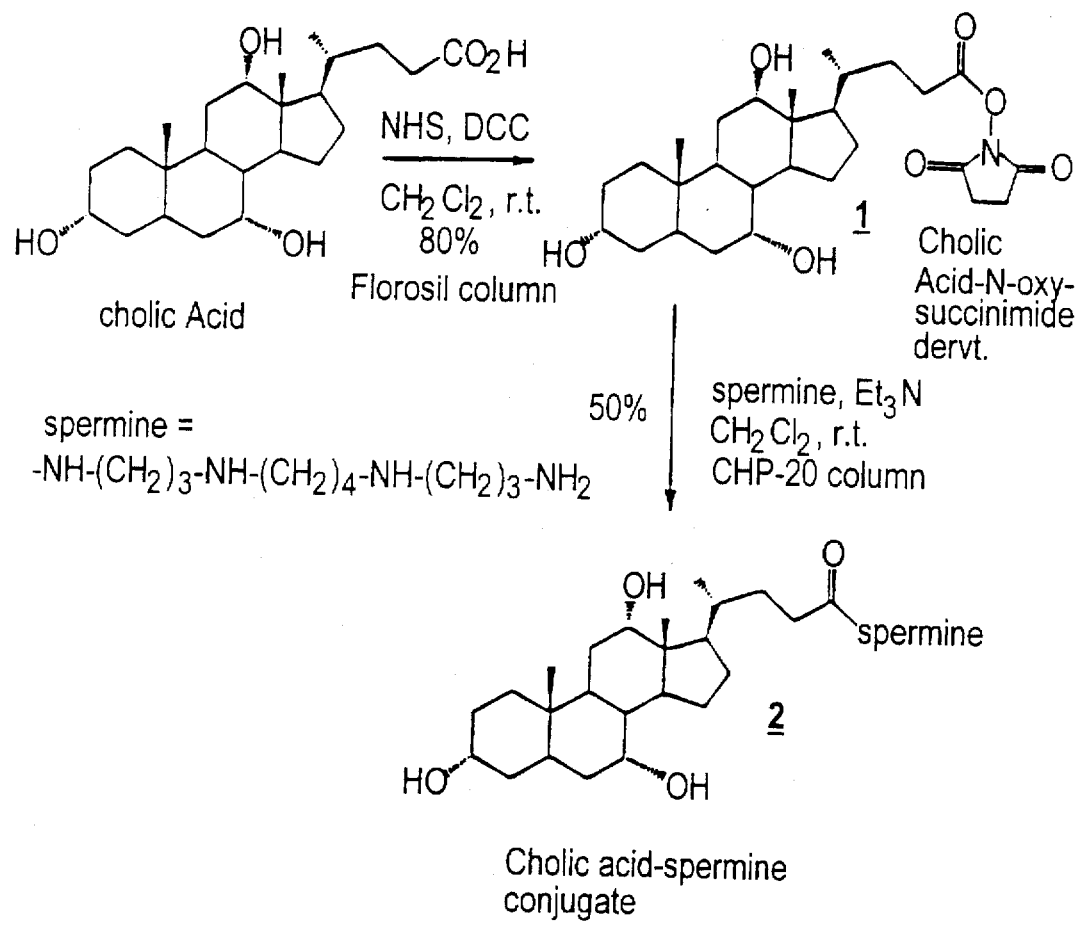
FIG. 5 illustrates the synthetic scheme for the preparation of 3α,7α,12α-trihydroxy-5β-cholan-24-oic acid, N-(4,9-diaza-12-aminododecyl)amide (may also be referred to as the cholic acid-spermine conjugate, Compound B).

10. Synthesis of 3α,7α,12α-Trihydroxy-5β-cholan-24-oic Acid, N-Oxysuccinimide (Comp. 1 of FIG. 5)

A mixture of dry cholic acid (8.16 g, 20 mmol), dicyclohexeylcarbodimide (4.33 g, 21 mmol) and N-hydroxysuccinimide (2.417 g, 21 mmol) is stirred in dry methylene chloride (200 mL) at room temperature for 6 h. The reaction mixture is filtered, and the filtrate concentrated. The residue is purified by flash chromatography through florosil (EtOH:$CH_2Cl_2$ 1:19) giving 8 g (79% yield) of compound 1 as a white foam (mp 92°–95° C.). TLC (EtOH:$CH_2Cl_2$ 1:19) $R_f$ 0.6. IR (KBr): 3385 (br), 2933, 2861, 2118, 1814, 1783, 1738, 1376, 1208, 1073 cm$^{-1}$. $^1$H NMR ($CDCl_3$): δ3.94 (s, 1H), 3.81 (s, 1H), 3.42 (m, 1H), 2.82 (br, 4H), 2.30–1.00 (m, 24H), 0.99 (d, 1H, J=5.7 Hz), 0.862 (s, 3H), 0.67 (s, 3H). Fab MS: 528 (M+Na)$^+$.

10.1. Preparation of 3α,7α,12α-Trihydroxy-5β-cholan-24-oic Acid, N-(4,9-Diaza-12-aminododecyl)amide (Comp. B of Table 1 or Comp. 2 of FIG. 5)

To a stirred solution of spermine (303 mg, 1.5 mmol) and triethylamine (1 mL) in anhydrous methylene chloride (20 mL), N-oxysuccinimidocholate 1 (505 mg, 1 mmol) in anhydrous methylene chloride (20 mL) is added dropwise during a 10 min period. The solution is then stirred for 3 h at room temperature. The reaction mixture is filtered and filtrate concentrated. The residue is purified by flash chromatography using CHP-20 reverse-phase resin (water and then 75% aqueous MeOH), affording 2 (360 mg, 52% yield) as a white foam (mp 140°–145° C.). TLC (MeOH:$CH_2Cl_2$:isopropylamine 4.5:4.5:1) $R_f$ 0.4. IR (KBr): 3350 (br), 2934, 2859, 1685, 1644, 1547, 1449, 1377, 1234, 1207, 1078, 1046 cm$^{-1}$. $^1$H NMR (DMSO-$d_6$ and 2 drops of $D_2O$): δ3.78 (s, 1H), 3.61 (s, 1H), 3.40–2.80 (m, 9H), 2.42–0.77 (m, 42H), 0.55 (s, 3H). Fab MS: 615 (M+Na)$^+$.

11. Synthesis of 3α,12α-Dihydroxy-7-deoxy-5β-cholan-24-oic Acid, N-Oxysuccinimide A mixture of dry deoxycholic acid (2.356 g, 6 mmol), dicyclohexeylcarbodimide (1.444 g, 7 mmol) and N-hydroxy-succinimide (0.806 g, 7 mmol) are stirred in dry methylene chloride (200 mL) at room temperature for 6 h. The reaction mixture is filtered, and the filtrate concentrated. The residue is purified by flash chromatography through florosil (EtOH: $CH_2Cl_2$ 1:19), affording 1.764 g (60% yield) of the title compound as a white foam (mp 75°–80° C.). TLC (EtOH: $CH_2Cl_2$ 1:9) $R_f$ 0. 5. IR (KBr): 3364 (br), 2934, 2862, 1814, 1783, 1738, 1655, 1627, 1449, 1376, 1208, 1068 cm$^{-1}$. $^1$H NMR ($CDCl_3$): δ3.97 (s, 1H), 3.62 (m, 1H), 2.82 (br, 4H), 2.70–0.83 (m, 30H). 0.67 (s, 3H). Fab MS: 512 (M+Na)$^+$.

11.1. Preparation of 3α,12α-Dihydroxy-7-deoxy-5β-cholan-24-oic Acid, N-(12-Aminododecane) amide To a stirred solution of dodecan-1,12-diamine (600 mg, 3 mmol) and triethylamine (1 mL) in anhydrous methylene chloride (25 mL), N-oxysuccinimidodeoxycholate (9 80 m g, 2 mmol) in anhydrous methylene chloride (25 mL) is added dropwise during 10 minute period. The contents are stirred for 14 h at room temperature. The reaction mixture is filtered, and the filtrate concentrated. The residue is purified by flash chromatography u sing CHP-20 reverse-phase resin (20%, 40%, 60%, 800% aqueous MeOH and then MeOH) to give the title compound (575 mg, 50% yield) as a white foam (mp 118°–120° C.). TLC (MeOH:$CH_2Cl_2$:isopropylamine 4.5:4.5:1) Rf 0.8. IR (KBr) : 3365 (br), 2928, 2857, 1654, 1647, 1534, 1449, 1376, 1044 cm$^{-1}$. $^1$H NMR ($CDCl_3$): δ3.97 (s, 1H), 3.62 (m, 1H), 3.21 (q, 1H, J=6.6 Hz), 2.70–1.00 (m, 48H), 0.98 (d, 1H, J=6.0 Hz), 0.90 (d, 1H), 0.67 (s, 3H). Fab MS: 622 (M+2Na)$^+$.

12. Preparation of Bis(glycosylated)cholic Acid-Spermine Conjugate (Comp. C of Table 1 or Comp. 7 of FIG. 6)

12.1. Synthesis of 3α-Hydroxy-7α,12α-di(2',3',4',6'-tetra-O-benzyl-1'α-glucosyl)-5β-cholan-24-oic Acid, N-Oxysuccinimide (Comp. 5 of FIG. 6)

A solution of dry 7α,12α-di-(2',3',4',6'-tetra-O-benzyl-1'α-glucosyl)-5β-cholan-24-oic acid (1.452 g, 1 mmol), N-hydroxysuccinimide (126 mg, 1.1 mmol) and DCC (226 mg, 1.1 mmol) in dry methylene chloride is stirred at room temperature for 3 h. The reaction mixture is filtered, and the filtrate concentrated. The residue is purified by flash chromatography through a column of florosil (EtOH:$CH_2Cl_2$ 1:19) to give 1.40 g (90% yield) of comp. 5 as a white foam (mp 63°–65° C.). TLC (EtOH:$CH_2Cl_2$ 1:19) $R_f$ 0.5. IR (KBr): 3062, 3030, 2928, 2863, 2117, 1813, 1784, 1740, 1685, 1496, 1453, 1363, 1206, 1070 cm$^{-1}$. $^1$H NMR ($CDCl_3$): δ7.40–6.90 (m, 40H), 5.10–3.10 (m, 33H), 2.80 (br s, 4H), 2.62–0.84 (m, 30H), 0.73 (s, 3H). Fab MS: 1572 (M+Na)$^+$.

12.2. Preparation of 3α-Hydroxy-7α,12α-di(2',3',4',6'-tetra-O-benzyl-1'α-glucosyl)-5β-cholan-24-oic Acid, N-(4,9-Diaza-12-aminododecyl)amide (Comp. 6 of FIG. 6)

To a stirred solution spermine (0.808 g, 4 mmol) and triethylamine (3 mL) in dry methylene chloride (50 mL), comp. 5 (5.16 g, 3.33 mmol) in methylene chloride (50 mL) is added and stirred for 4 h. The reaction mixture is filtered, and the filtrate is washed with water (2×50 mL), dried ($Na_2SO_4$), and concentrated. The residue is purified by flash chromatography through a column of CHP-20 reverse-phase resin (water, then methanol) to afford comp. 6 (4.9 g, 85% yield) as a white foam (mp 58°–60° C.). TLC (MeOH:$CH_2Cl_2$:isopropylamine 4.5:4.5:1) $R_f$ 0.2. IR (KBr): 3063, 3030, 2928, 2863, 1655, 1628, 1496, 1452, 1362, 1208, 1147, 1070, 1028 $cm^{-1}$. $^1H$ NMR ($CDCl_3$): δ7.40–6.90 (m, 40H), 6.62 (br s, 1H), 5.03–3.20 (m, 33H), 3.00–0.86 (m, 55H), 0.72 (s, 3H). Fab MS: 1659 (M+Na)$^+$. Anal. Calc. for $C_{102}H_{132}O_{14}N_4 \cdot H_2O$: C, 74.16; H, 8.19; N, 3.35. Found: C, 73.53; H, 8.24; N, 3.72.

12.3. Preparation of 3α-Hydroxy-7α,12α-di(1'α-glucosyl)-5β-cholan-24-oic Acid, N-(4,9-Diaza-12-aminododecyl) amide (Comp. C)

To a solution of comp. 6 (2.455 g, 1.5 mmol) and 1N aqueous HCl (25 mL) in THF (50 mL), 20% palladium hydroxide on carbon (2 g, Perlman's catalyst) is added. The mixture is subjected to hydrogenalysis at 50 psi for 6 h. The reaction mixture is filtered through sand and membrane filter and concentrated. The residue is dissolved in water (5 mL) and filtered. The filtrate is purified by flash chromatography through a column of CHP-20 reverse-phase column (water, followed by MeOH:Water 1:9) to give 1.078 g (70% yield) of C as a white foam (mp 83°–85° C.). TLC (trifluoroacetic acid:water 1:9) $R_f$ 0.35. IR (KBr): 3365 (br), 2938, 2867, 1638, 1629, 1561, 1545, 1459, 1150, 1075, 1048, 1025 $cm^{-1}$. $^1H$ NMR ($D_2O$): δ5.06 (d, 1H, J=3.6 Hz), 4.85 (d, 1H, J=3.6 Hz), 3.95 (br s, 1H), 3.78–2.88 (m, 21H), 2.28–0.76 (m, 46H), 0.64 (s, 3H). Fab MS: 940 (M+Na)$^+$.

Anal. Calc. for $C_{36}H_{84}O_{14}N_4 \cdot 3HCl \cdot 5H_2O$: C, 49.66; H, 8.52; N, 5.04; Cl, 9.44. Found: C, 49.68; H, 8.60; N, 5.06; Cl, 9.65.

13. Synthesis of Various (Polyaminoalkyl)amides of Deoxycholic and Chenodeoxycholic Acids 13.1. Preparation of 3α,12α-Dihydroxy-7-deoxy-5β-cholan-24-oic Acid, N-(3,6,9-Triaza-11-aminoundecyl) amide (Comp. F of Table 1)

To a solution of tetraethylene-pentamine (0.378 g, 2.5 mmol) and triethylamine (0.3 mL) in DMF (5 mL) is added dropwise over 10 min the N-oxysuccinimidodeoxycholate (1.0 g, 2 mmol) in 5 mL of DMF. The solution is stirred overnight at room temperature, poured into water (20 mL). The precipitate obtained is washed with cold water (50 mL), dissolved in 10 mL of 2% HCl, and filtered. The solution is poured over a CHP-20 reverse phase column and eluted using a 40–80% MeOH in water solvent gradient system to afford 1.1 g (72% yield) of the trihydrochloride, pentahydrate form of the title compound, as a white powder after lyophilization (m.p. 130°–132° C.). TLC (MeOH:i-PrNH$_2$:DCM 2:2:6) $R_f$ 0.6. IR (KBr): 3419, 2934, 1642 (CONH—), 1553, 1454, 1038 $cm^{-1}$. $^1H$ NMR ($D_2O$): δ3.88 (s, 1H), 2.9–3.3 (m, 16H), 1.2–2.4 (m, 42H), 0.88 (d, 3H), 0.78 (s, 3H), 0.55 (s, 3H). Fab MS:696 (Base-3HCl+Na$^+$). Anal. Calc. for $C_{32}H_{61}N_5O_3 \cdot 3HCl \cdot 5H_2O$: C 50.3; H 9.69; N 9.17; Cl 13.95. Found: C 51.5; H 9.04; N 10.1; Cl 10.9.

13.2. Preparation of 3α,12α-Dihydroxy-7-deoxy-5β-cholan-24-oic Acid, N-(3,6,9,12-Tetraaza-14-aminotetradecyl)amide (Comp. G of Table 1)

To a solution of pentaethylenehexamine (0.58 g, 2.5 mmol) and triethylamine (0.3 mL) in DMF (5 mL) is added dropwise over 10 min the N-oxysuccinimidedeoxycholate (1.0 g, 2 mmol) in 5 mL of DMF. The solution is stirred overnight at room temperature, then poured into water (50 mL) to give a precipitate. The liquid phase is decanted. The semi-solid precipitate is washed successively with cold 5% NaOH (10 mL×2) and water (10 mL), dissolved in 10 mL of 10% acetic acid, and purified by flash chromatography through a CHP-20 reverse-phase column using a 40–100% MeOH in water solvent gradient system. The fractions containing product are combined, evaporated at reduced pressure, dissolved in 2% aqueous HCl solution, and lyophilized to afford 0.75 g (42% yield) of the title compound as a white powder (m.p. 140°–142° C.). TLC (MeOH:i-PrNH$_2$:DCM 2:2:6) $R_f$ 0.65. IR (KBr): 3425, 2932, 1770 (COOH), 1643 (CONH), 1552 (COO$^-$), 1454, 1032 $cm^{-1}$.

$^1H$ NMR ($D_2O$): δ3.92 (s, 1H), 2.6–3.6 (m, 20H), 1.0–1.6 (m, 30H), 0.83 (d, 3H), 0.75 (s, 3H), 0.55 (s, 3H). Fab MS: 863 (M+H$^+$). Anal. Calc. for $C_{34}H_{66}N_6O_3 \cdot 2HCl \cdot 3AcOH$: C 55.8; H 9.28; N 9.70; Cl8.2. Found: C 59.0; H 9.40; N 8.3; Cl 6.6.

13.3. Preparation of 3α,7α-Dihydroxy-12-deoxy-5β-cholan-24-oic Acid, N-(4,9-Diaza-12-aminododecyl)amide (Comp. H of Table 1)

To a solution of spermine (0.8 g, 2 mmol) and triethylamine (0.3 mL) in 5 mL of DMF is added dropwise the N-oxysuccinimidechenodeoxycholate (1.0 g, 2 mmol) in 5 mL of DMF. The mixture is stirred overnight at room temperature, then poured into DCM (100 mL). The precipitate of the hydroxysuccinimide is filtered, and the filtrate is evaporated to give a liquid phase, which is poured into water (100 mL). The precipitate of the product is obtained. It is dissolved in MeOH (5 mL) and passed through a CHP-20 reverse-phase column. A 300 MeOH in water solvent system is used to elute the product. The solvent is removed by evaporation, and the residue is dissolved in 1 mL of trifluoroacetic acid. The resulting solution is diluted up to 10 mL with water, filtered, and the filtrate subsequently lyophilized to afford 0.9 g (50% yield) of a solid (m.p. 96°–100° C.). The product is soluble in water. A 5% solution of the trifluoroacetate salt of the chenodeoxycholic acid-spermine conjugate is stable at room temperature over about 12–24 h, after which a precipitate of the base separates as a slurry. TLC (MeOH:i-PrNH$_2$:DCM 1:1:2) $R_f$ 0.7. IR (KBr): 3406, 2939, 2869, 1778 (COOH), 1680 (CONH—), 1553, 1458, 1196, 834, 722 $cm^{-1}$. $^1H$ NMR ($D_2O$): δ3.75 (s, 1H), 3.4 (s, 1H), 2.8–3.15 (m, 12H), 2.2–1.2 (m, 39H), 0.9 (d, 3H), 0.86 (s, 3H), 0.55 (s, 3H). Fab MS: (M+Na$^+$)=598. Anal. Calc. for $C_{34}H_{64}N_4O_3 \cdot 3CF_3COOH$: C 52.5; H 7.29; N 6.09. Found: C 53.5; H 7.20; N 4.95.

13.4. Preparation of 3α,7α-Dihydroxy-12-deoxy-5β-cholan-24-oic Acid, N-(3,6,9-Triaza-12-aminoundecyl) amide (Comp. I of Table 1)

To a solution of the tetraethylene-pentaamine base (1.90 g, 10 mmol) and triethylamine (1.0 g, 10 mmol) in 100 mL of DCM, N-oxysuccinimidechenodeoxycholate (2.46 g, 5 mmol) in DCM (50 mL) is added and the solution is stirred 48 h at room temperature. The reaction mixture is diluted with 100 mL of DCM, washed with water (2×100 mL), dried over sodium sulfate and evaporated to dryness. The residue is dissolved in 25 mL of 10% acetic acid, filtered and the clear filtrate is purified on CHP-20 column in MeOH-water. At 40%–80% of MeOH the product is eluted. The combined fractions are acidified by 10% HCl (5 mL) and the methanol is distilled off under vacuum. The rest of the water solution is removed by lyophilization to give 2.84 g (77% yield, m.p. 200°–203° C. decomp.) of the pentaaminotetraethyleneamide of the chenodeoxycholic acid. TLC (MeOH:i-PrNH$_2$:DCM) $R_f$ 9.8. IR (KBr): 3350, 2974, 1665, 1635, 1551, 1539, 1460, 1470, 1377, 1077, 978, 766 $cm^{-1}$. $^1H$ NMR (D$_2$O)=δ3.378 (s, 1H), 2.9–3.4 (m, 16H), 1.8–1.2 (m, 39H), 0.85 (d, 3H), 0.76 (s, 3H), 0.55 (s, 3H). Fab MS: (M+H$^+$)=564.

Anal. Calc. for C$_{32}$H$_{61}$N$_5$O$_3$.4HCl.2H$_2$O: C 51.54; H 9.26; N 9.39; Cl 19.06. Found: C 50.48; H 8.84; N 8.86; Cl 19.7.

13.5. Preparation of 3α,7α,12α-Trihydroxy-5β-cholan-24-oic Acid, N-(3,6,9,-Triaza-12-aminoundecyl)amide (Comp. J of Table 1)

To a solution of the tetraethylenepentamine (0.8 g, 5 mmol) and TEA (0.3 g, 3 mmol) in DCM (25 mL) the N-oxysuccinimidecholate (1.0 g, 2.0 mmol) is added. A clear solution is stirred at room temperature for 48 h, the reaction mixture is diluted with DCM (100 mL), washed with cold water (20 mL), dried over sodium sulfate and evaporated to dryness. The residue is dissolved in 20 mL of 5% AcOH. A purification is carried out on a CHP-20 reverse phase column in MeOH-water. The product runs at 40%–80% of MeOH. The fractions containing target compound are combined, methanol is distilled off, and 10 mL of 10% HCl is added. Lyophilization gives 0.70 g (50% yield) of the pure substance, m.p. 135°–140° C. TLC (MeOH:i-PrNH$_2$:DCM-1:1:3) R$_f$ 0.8. IR (KBr): 3406, 2937, 1640 (C=O), 1556, 1453, 1376, 1023 cm$^{-1}$. $^1$H NMR (D$_2$O): δ3.8 (s, 1H), 3.65 (s, 1H), 3.0–3.3 (m, 16H), 2.0–1.1 (m, 26H), 0.78 (d, 3H), 0.72 (s, 3H), 0.48 (s, 3H). Fab MS: (M+H$^+$)580. Anal. Calc. for C$_{32}$H$_{61}$N$_5$O$_4$.5HCl: C 50.4; H 8.66; N 9.18; Cl 23.29. Found: C 47.27; H 8.31; N 8.57; Cl 25.63.

13.6. Preparation of 3α,7α,12α-Trihydroxy-12-deoxy-5β-cholan-24-oic Acid, N-(3,6,9,12-Tetraaza-14-aminotetradecyl)amide (Comp. K of Table 1)

To a solution of the pentaethylenehexamine (0.9 g, 5.5 mmol) and triethylamine (0.3 g, 3 mmol) in DCM (10 mL) the neat N-oxysuccinimidecholate (1.0 g, 2.0 mmol) is added with stirring at room temperature. The reaction mixture is stirred at room temperature for 48 h. At the end of this period, the reaction mixture turns into a semisolid, which is diluted with 150 mL of DCM, washed with cold water (2×50 mL), dried and distilled to dryness, dissolved in 10 mL of 10% AcOH, filtered from insoluble material, and purified on a reverse-phase column CHP-20 with methanol-water. The product runs at 40%–70% of methanol. The combined fractions containing product is distilled from methanol. Afterwards, 10% HCl (5 mL) is added. After lyophilization, 0.96 g (55% yield) is obtained (m.p. 230° C., decomp.). TLC (DCM:MeOH:iPrNH$_2$-5:1:1) R$_f$ 0.85. IR (KBr): 3393, 2937, 1646 (C=O), 1550, 1483, 1376, 1072, 1028, 774 cm$^{-1}$. $^1$H NMR (D$_2$O): δ3.83 (s. 1H), 3.67 (s. 1H), 3.1–3.5 (m. 21H), 2.0–1.4 (m. 26H), 0.78 (d. 3H), 0.68 (s. 3H), 0.48 (s. 3H). Fab MS: (M+H$^+$): 623. Anal. Calc. for C$_{32}$H$_{61}$N$_5$O$_4$.5HCl: C 50.4; H 8.66; N 9.18; Cl 23.29. Found: C 47.27; H 8.31; N 8.57; Cl 25.63.

13.7. Preparation of 3α-Hydroxy-7α,12α-di(1'α-glucosyl)-5β-cholan-24-oic Acid, N-(3,6,9,12-Tetraaza-14-aminotetradecyl)amide (Comp. L of Table 1)

13.7.1 Preparation of 3α-Hydroxy-7α, 12α-di(2',3',4',6'-tetra-O-benzyl-1'α-glucosyl)-5β-cholan-24-oic Acid, N-(3, 6,9,12-Tetraaza-14-aminotetradecyl)amide To a stirred solution of pentaethylenehexamine (367 mg 1.5 mmol) and triethylamine (2 mL) in dry methylenechloride (50 mL), N-oxysuccinimide-7α,12α-di(perbenzylglucosyl)cholate (1.549 g, 1 mmol) in methylene chloride (50 mL) is added dropwise and stirred for 48 h. The reaction mixture is filtered, and the filtrate is concentrated. The residue is purified on flash chromatography over CHP-20 reverse phase resin (eluants, water and then gradually increasing to 90% methanol; product is obtained from 90% methanol in water fractions) affords the title compound (950 mg, 57% yield) as a white foam (m.p. 78°–80° C.). TLC (solvent-MeOH:CH$_2$Cl$_2$:Isopropylamine 4:4:2) R$_f$ 0.1. IR (KBr): 3500 (br), 3086, 3061, 3030, 2929, 2864, 1699, 1652, 1453, 1363, 1155, 1071, 1028 cm$^{-1}$. $^1$H NMR (CDCl$_3$): δ7.40–6.90 (m, 40H), 5.03–3.10 (m, 33H), 2.90–0.66 (m, 65H). Fab MS: 1674 (M+Na)$^+$.

13.7.2 Preparation of 3α-Hydroxy-7α,12α-di(1'α-glucosyl)-5β-cholan-24-oic Acid, N-(3,6,9,12-Tetraaza-14-aminotetra-decyl)amide To a solution of the compound from above (333 mg, 0.2 mmol) and 1N aqueous HCl (3 mL, 3 mmol) in THF and water (2:1, 30 mL), 20% palladium hydroxide on carbon (300 mg, Perlman's catalyst) is added and the mixture is subjected to hydrogenolysis at 50 psi for 15 h. The reaction mixture is filtered through sand and membrane filter and then concentrated. The residue is dissolved in water (5 ml) and filtered. The filtrate is purified on flash chromatography over CHP-20 reverse phase column (water, followed by MeOH:Water=1:19, 1:4 and 2:3; product is found in 20% methanol in water fractions) to give 110 mg (40% yield) of the desired compound as a white foam (mp 180°–82° C.). TLC (solvent-Trifluoroacetic acid:Water 1:9) R$_f$ 0.3. IR (KBr): 3394, 2934, 2867, 1652, 1647, 1636, 1558, 1541, 1027 cm$^{-1}$. $^1$H NMR (D$_2$O): δ5.09 (d, 1H, J=3.6 Hz), 4.86 (d, 1H, JjJJ-3.6 Hz), 3.95 (brs, 1H), 3.80–255 (m, 15H), 2.30–0.65 (m, 56H). Fab MS: 970 (M+Na)$^+$. Anal. Calc. for C$_{46}$H$_{86}$O$_{14}$N$_6$.4HCl: C 50.55; H 8.30; N 7.69; Cl 12.97. Found: C 50.67; H 8.71; N 6.70; Cl 11.65.

13.8. Preparation of 3α-Hydroxy-7α,12α-di(1'α-glucosyl)-5β-cholan-24-oic Acid, N-(3,6,9-Triaza-12-amino-undecyl)amide (Comp. M of Table 1)

13.8.1. Preparation of 3α-Hydroxy-7α,12α-di-(2',3',4',6'-tetra-O-benzyl-1'α-glucosyl)-5β-cholan-24-oic Acid, N-(3, 6,9-Triaza-12-aminoundecyl)amide To a stirred solution of tetraethylenepentamine (285 mg, 1.5 mmol) and triethylamine (2 mL) in dry methylene chloride (50 mL), N-oxysuccinimide-7α,12α-di(perbenzylglucosyl)cholate (1.549 g, 1 mmol) in methylene chloride (50 mL) is added dropwise and stirred for 48 h. The reaction mixture is filtered, and the filtrate is concentrated. The residue is purified on flash chromatography over CHP-20 reverse phase resin (eluants, water and then gradually increasing to 90% methanol; product is obtained from 90% methanol in water fractions) to afford the title compound (1 g, 63.8% yield) as a white foam (mp 74°–760° C.). TLC (solvent-MeOH:CH$_{2}$:isopropylamine 4:4:2) R$_f$ 0.1. IR (KBr): 3365, 3086, 3061, 3029, 2925, 2864, 1699, 1653, 1496, 1453, 1155, 1070, 1028 cm$^{-1}$. $^1$H NMR (CDCl$_3$): δ7.40–6.95 (m, 40H), 5.10–3.20 (m, 33H), 2.82–0.82 (m, 57H), 0.72 (s, 3H). Fab MS: 1651 (M+Na)$^+$.

13.8.2. Preparation of 3α-Hydroxy-7α,12α-di-(1'α-glucosyl)-5β-cholan-24-oic Acid, N-[3,6,9,-Triaza-12-aminoundecyl)amide To a solution of the above compound (486 mg, 0.3 mmol) and 1N aqueous HCl (4 mL, 3 mmol) in THF and water (2:1, 30 mL), 20% palladium hydroxide on carbon (400 mg, Perlman's catalyst) is added and the mixture is subjected to hydrogenolysis at 50 psi for 15 h. The reaction mixture is filtered through sand and membrane filter and concentrated. The residue is dissolved in water (5 mL) and filtered. The filtrate is purified on flash chromatography over CHP-20 reverse phase column (water followed by MeOH:water= 1:19, 1:4 and 2:3; product is found in 20% methanol in water fractions) to give 160 mg (50% yield) of the desired compound as white foam (m.p. 151°–53° C.). TLC (solvent-Trifluoroacetic acid:water 1:9) R$_f$ 0.3. IR (KBr): 3390, 2938, 2869, 1652, 1647, 1636, 1541, 1457, 1251, 1150, 1073, 1026 cm$^{-1}$. $^1$H NMR (D$_2$O): δ5.09 (br s, 1H), 4.86 (br s, 1H), 4.00 (m, 2H), 3.85–2.60 (m, 16H), 2.30–0.75 (m, 49H) and 0.66 (s, 3H). Fab MS: 927 (M+Na)$^+$. Anal. Calc. for C$_{44}$H$_{81}$O$_{14}$N$_5$.3HCl: C 52.14; H 8.35; N 6.91; Cl 10.49. Found: C 52.41; H 8.75; N 5.21; Cl 9.49.

13.9. Preparation of 3α-Hydroxy-7,12-dideoxy-5β-cholan-24-oic acid, N-(3,6,9,12-Tetraaza-14-aminotetrodecyl) amide (Comp. N of Table 1)

N-oxysuccinimidelithocholate (1.0 g, 2.1 mmol) is added to pentaethylenehexamine (0.73 g, 3.2 mmol) and triethylamine (0.21 g, 2.1 mmol). DCM (50 mL). The reaction mixture is stirred at room temperature for 48 h, diluted with DCM (100 mL), washed with water (2×100 mL), dried, and the solvent evaporated. The residue is dissolved in 50 mL of 10% AcOH over 5 h with vigorous stirring. The cloudy solution is purified on a reverse phase column in MeOH-water. After lyophilization, 1.1 g (60% yield) of the product is obtained (m.p. 94° C.). TLC (DCM:MeOH:iPrnH$_2$ 5:1:1) R$_f$ 0.65. IR (KBr): 3390, 2933, 2862, 1648 (C=O), 1555, 1402, 1075, 656 cm$^{-1}$. $^1$H NMR (D$_2$O): δ3.2–2.6 (m, 19H), 1.7–1.0 (m, 29H), 0.70(s, 6H), 0.42 (s, 3H). Fab MS: (597). Anal. Calc. for C$_{34}$H$_{66}$N$_6$O$_2$.5AcOH: C 59.3; H 9.66; N 9.44. Found. C 58.2; H 9.51; N 10.9.

14. Synthesis of 3β-Amino-7α,12α-di(1'α-glucosyl)-5β-cholan-24-oic Acid, N-(4,9-Diaza-12-amino-dodecyl) amide-HCl Salt 14.1. Preparation of 3β-Azido-7α,12α-di(2',3',4',6'-tetra-O-benzyl-1'α-glucosyl)-5β-cholan-24-oic Acid, N-Oxysuccinimide A solution of dry 3-0-azido-7α,12α-di-(2',3',4',6'-tetra-O-benzyl-1'α-glucosyl)-5β-cholan-24-oic acid (4.443 g, 3 mmol), N-hydroxysuccinimide (406 mg, 3.5 mmol) and DCC (722 mg, 3.5 mmol) in dry methylene chloride is stirred at room temperature for 3 h. The reaction mixture is filtered, and the filtrate concentrated. The residue is purified by flash chromatography through a florosil column (EtOAc:Hexane 1:3) to give 4 g (80% yield) of the activated cholate ester as a white foam (m.p. 64°–66° C.). TLC (EtOAc:Hexane 3:7) R$_f$ 0.3. IR (KBr): 3325, 3088, 3062, 3030, 2924, 2867, 2099, 1815, 1785, 1742, 1206, 1070 cm$^{-1}$. $^1$H NMR (CDCl$_3$): δ7.40–6.90 (m, 40H), 5.02 (q, 2H, J=3.6 Hz), 4.90–3.42 (m, 31H), 2.80 (br s, 4H), 2.62–0.90 (m, 30H), 0.75 (s, 3H).

14.2. Preparation of 3β-Azido-7α,12α-di(2',3',4',6'-tetra-O-benzyl-1'α-glucosyl)-5β-cholan-24-oic Acid, N-(4,9-Diaza-12-aminododecyl)amide To a stirred solution of spermine (0.303 g, 1.5 mmol) and triethylamine (3 mL) in dry methylene chloride (75 mL), compound from 14.1 (1.579 g, 1 mmol) in methylene chloride (75 mL) is added and stirred for 4 h. The reaction mixture is filtered, and the filtrate is washed with water (2×50 mL), dried (Na$_2$SO$_4$), and concentrated. The residue is purified by flash chromatography through a CHP-20 reverse-phase resin (eluant: water and then methanol) to afford the title compound (1.46 g, 86% yield) as a white foam (m.p. 60°–62° C.). TLC (MeOH:CH$_2$Cl$_2$: isopropylamine 4.5:4.5:1) R$_f$ 0.5. IR (KBr): 3432 (br), 3087, 3062, 3030, 2925, 2865, 2098, 1670, 1663, 1656, 1640, 1630, 1496, 1452, 1364, 1071, 1028 cm$^{-1}$. $^1$H NMR (CDCl$_3$): δ7.40–6.90 (m, 40H), 6.30–6.10 (m, 1H), 5.04–3.10 (m, 33H), 2.80–0.83 (m, 55H) 0.73 (s, 3H).

14.3. Preparation of 3β-Amino-7α,12α-di(2',3',4',6'-tetra-O-benzyl-1'α-glucosyl)-56-cholan-24-oic Acid, N-(4,9-Diaza-12-aminododecyl)amide To a stirred mixture of the compound of 14.2 (0.999 g, 0.6 mmol) and Raney Ni (500 mg) in ethanol (10 mL) is added dropwise over 10 min a hydrazine hydrate (0.2 mL, 4 mmol) in ethanol (10 mL). The mixture is stirred for 2 h, after which it is filtered. The filtrate is concentrated under vacuum (aspirator pump). The residue is washed with water (3×50 mL) and dried under vacuum to give the desired 3-amino compound (920 mg, 94%) as a white foam (m.p. 55°–57° C.). TLC (MeOH:CH$_2$Cl$_2$:isopropylamine 4.5:4.5:1) R$_f$ 0.5. IR (KBr): 3415 (br), 3087, 3062, 3029, 2925, 2864, 1669, 1662, 1654, 1647, 1630, 1496, 1453, 1362, 1086, 1070, 1028 cm$^{-1}$. $^1$H NMR (CDCl$_3$): δ7.40–6.90 (m, 40H), 6.30–6.10 (m, 1H), 5.00–3.00 (m, 33H), 2.80–0.78 (m, 55H), 0.66 (s, 3H).

14.4. Preparation of 3β-Amino-7α,12α-di(1'α-glucosyl)-5β-cholan-24-oic Acid, N-(4,9-Diaza-12-aminododecyl) amide HCl Salt To a solution of compound of 14.3 (0.91 g, 0.56 mmol) and 1N aqueous HCl (8 mL, 8 mmol) in THF (25 mL) and water (10 mL) is added 20% palladium hydroxide on carbon (0.9 g, Perlman's catalyst), and the mixture is subjected to hydrogenolysis at 50 psi for 14 h. The reaction mixture is filtered through sand and a membrane filter, then concentrated. The residue is dissolved in water (5 mL) and filtered. The filtrate is purified by flash chromatography through a CHP-20 reverse-phase column (eluant: water, followed by 2% MeOH in water) to give 260 mg (44% yield) of the title compound as a white powder (m.p. 125°–127° C.). TLC (trifluoroacetic acid:water 1:9) R$_f$ 0.3. IR (KBr): 3395 (br), 2940, 1640, 1630, 1450, 1150, 1075, 1047, 1023 cm$^{-1}$. $^1$H NMR (D$_2$): δ5.09 (br s, 1H), 4.87 (br s, 1H), 3.98 (br s, 1H), 3.78–2.88 (m, 21H), 2.60–1.00 (m, 40H), 0.91 (s, 3H), 0.82 (d, 3H, J=5.1 Hz), 0.66 (s, 3H).

Hence, the present invention also contemplates various compounds selected from non-glycosylated, monoglycosylated, and bis(glycosylated) bile acid-poly (aminoalkylene) or aminoarylene conjugates, including, in particular, 3α,12α-dihydroxy-7-deoxy-5β-cholan-24-oic acid, N-(4,9-diaza-12-aminododecyl)amide (deoxycholicacid-spermine conjugate); 3α-hydroxy-7α,12α-di(1'α-glucosyl)-5β-cholan-24-oic acid, N-(4,9-diaza-12-aminododecyl)amine (bis(glycosylated)cholic acid-spermine conjugate); 3α-hydroxy-12α-(1'α-glucosyl)-7-deoxy-5β-cholan-24-oic acid, N-(4,9-diaza-12-aminododecyl)amide (12α-(O-glucosyl)deoxycholic acid-spermine conjugate); 3α-hydroxy-7α-(1'α-glucosyl)-12-deoxy-5β-cholan-24-oic acid, N-(4,9-diaza-12-aminododecyl)amide (7α-(O-glucosyl)chenodeoxycholic acid-spermine conjugate); 3α,7α,12α-trihydroxy-5β-cholan-24-oic acid, N-(4,9-diaza-12-aminododecyl)amide; 3α,12α-dihydroxy-7α-deoxy-5β-cholan-24-oic acid, N-(12-aminododecyl)amide (deoxycholic acid-1,12-diaminododecane conjugate); 3α,12α-dihydroxy-7-deoxy-5β-cholan-24-oic acid, N-(12-aminododecyl)amide; 3α-hydroxy-7α,12α-di(2',3',4',6'-tetra-O-benzyl-1'α-glucosyl)-5β-cholan-24-oic acid, N-(4,9-diaza-12-aminododecyl)amide; 3α,12α-dihydroxy-7-deoxy-5β-cholan-24-oic acid, N-(3,6,9-triaza-11-aminoundecyl)amide; 3α,12α-dihydroxy-7-deoxy-5β-cholan-24-oic acid, N-(3,6,9,12-tetraaza-14-aminotetradecyl)amide; 3α,7α-dihydroxy-12-deoxy-5β-cholan-24-oic acid, N-(4,9-diaza-12-aminododecyl)amide; 3β- and 3α-amino-7α,12α-di(1'α-glucosyl)-5-cholan-24-oic acid, N-(4,9-diaza-12-aminododecyl)amide; 3β- and 3α-amino-7α,12α-di(2',3',4',6'-tetra-O-benzyl-1'α-glucosyl)-5β-cholan-24-oic acid, N-(4,9-diaza-12-aminododecyl)amide, intermediates in their syntheses described herein, and their pharmaceutically acceptable salts.

15. Biological Activity-Determination of MIC Against Bacteria

The results shown in Table 1 demonstrate that the compounds of the present invention exhibit activity useful in the treatment or prevention of infections.

The biological activity of the present compounds is demonstrated as follows. To demonstrate their anti-infective properties, the minimum inhibitory concentration (MIC) for many of the novel compounds is obtained against a variety of antibiotic indicator strains of bacteria. Antibiotic indicator strains *Escherichia coli* strain 25922, *Enterococcus faecalis* 29212, *Pseudomonas aeruginosa* 27853, and *Staphylococcus aureus* 29213 are obtained from the American Type Tissue Culture Collection (ATCC) in Rockville, Md. The cystic fibrosis isolate, *Pseudomonas aeruginosa* 39324, is also obtained from ATCC. Bacteria are routinely cultivated in cation-supplemented Mueller-Hinton broth (CAMHB) or agar at 37° C.

The minimum inhibitory concentration (MIC) of glycosylated and non-glycosylated steroidal polyamines for antibiotic indicator strains is determined by dissolving the test compounds in deionized water to a final concentration of 1 mg per mL. Those compounds that are poorly soluble in water are dissolved in acetic acid, dried in a stream of nitrogen gas, and dissolved in deionized water to a final concentration of 1 mg per mL. These solutions are sterilized by filtration through 0.22 micron syringe filters.

Stock solutions of individual compounds are serially diluted (two-fold) in sterile CAMHB in 96-well tissue culture dishes (Falcon) and inoculated with antibiotic indicator strains that are prepared as described below. All compounds are tested in duplicate at concentrations that ranged from 1.56 to 200 μg per mL.

Antibiotic indicator strains are grown in 5 mL of CAMHB for 3–4 h at 37° C. with shaking (200 rpm) on a New Brunswick rotary shaker. Bacteria are adjusted to a turbidity that matched a 0.5 McFarland standard (ca. 108 CFU per mL) in sterile 0.85% saline. These bacterial suspensions are diluted 1:20 in sterile 0.85% saline and 10 μL (ca. $5\times10^5$ CFU) of each suspension is used to inoculate individual wells of a 96 well plate that contained different concentrations of the test compounds. Following inoculation, the plates are sealed with plastic tape, incubated for 24 h at 37° C. and visually inspected for bacterial growth. CAMHB inoculated with each of the antibiotic test strains and uninoculated CAMBH plus each of the test compounds served as positive and negative controls. The MIC is defined as the lowest concentration of a compound that completely inhibited visual evidence of bacterial growth.

TABLE 1

Anti-Infective Properties Of Compounds

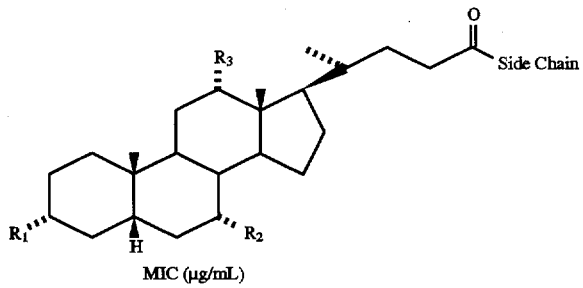

MIC (μg/mL)

| Cmpd No. | $R^1$ | $R^2$ | $R^3$ | Side Chain | *E. coli* 25922 | *P. aeurginosa* 27853 | *E. faecalis* 29212 | *S. aureus* 29213 | *P. aeruginosa* 39324 |
|---|---|---|---|---|---|---|---|---|---|
| A | α-OH | H | OH | spermine | 12.5 | 3.12 | 12.5 | 6.25 | 25 |
| B | α-OH | OH | OH | spermine | 200 | 100–200 | 200 | 50 | 100 |
| C | α-OH | α-D-Glc | α-D-Glc | spermine | 200 | 200 | >200 | 200 | — |
| D | α-OH | H | α-D-Gln | spermine | 100 | 100–200 | 200 | 50–100 | — |
| E | α-OH | α-D-Glc | H | spermine | 12.5 | 12.5 | 25 | 25 | 12.5 |
| F | α-OH | H | OH | pentamine | 100 | 100 | 100 | 25 | 100 |
| G | α-OH | H | OH | hexamine | 100 | 50 | 100 | 25 | 50–100 |
| H | α-OH | OH | H | spermine | 25 | 12.5 | 3.12 | 6.25 | 50–100 |
| I | α-OH | OH | H | pentamine | 25 | 50 | 25 | 12.5 | 50 |
| J | α-OH | OH | OH | pentamine | 75 | 75 | 18.7 | 37.5 | 37.5 |
| K | α-OH | OH | OH | hexamine | 75 | 75 | 15.7 | 37.5 | 75 |
| L | α-OH | α-D-Glc | α-D-Glc | hexamine | >200 | >200 | >200 | >200 | >150 |
| M | α-OH | α-D-Glc | α-D-Glc | pentamine | >200 | >200 | >200 | >200 | >150 |
| N | α-OH | H | H | hexamine | >200 | 200 | 200 | 50 | 200 |
| pentaethylene-hexamine | — | — | — | — | >200 | >200 | >200 | >200 | >150 |
| spermine | — | — | — | — | >200 | >200 | >200 | >200 | >150 |
| tetraethylene-pentamine | — | — | — | — | >200 | >200 | >200 | >200 | >150 |
| cholic acid sodium salt | — | — | — | — | >200 | >200 | >200 | >200 | >200 |
| deoxycholic acid sodium salt | — | — | — | — | >200 | >200 | >200 | >200 | >200 |

The nomenclature of compounds A to N has been provided earlier in this specification.

16. Augmentation Assay

The effect of the present compounds on the MIC of erythromycin, gentamicin and vancomycin for antibiotic indicator strains is determined, as described below.

Stock solutions 1–2 mg/mL of test compounds are prepared in distilled water, filter-sterilized through a 0.22 Am filter and diluted in CAMHB to the desired starting concentration. Aliquots of each test compound (0.1 mL), at 2× the final concentration, are added to the first rows of 96 well plates. The remaining wells of these plates are charged with 0.1 mL aliquots of each test compound at the desired final concentration. Subsequently, 0.1 mL of solutions of erythromycin, gentamicin, or vancomycin, prepared in CAMHB, are added to the first rows of these plates and serially diluted.

The wells are inoculated in duplicate with each of four antibiotic indicator strains prepared as described previously above. The final concentrations of antibiotics tested in these experiments range from 0.185–250 µg per mL. Plates containing each of the antibiotics serially diluted in CAMHB alone are also inoculated with antibiotic indicator strains to determine the MIC of erythromycin, gentamicin and vancomycin in the absence of the compounds of the invention. The plates are sealed with plastic tape, incubated in for 24 h at 37° C., visually inspected for bacterial growth. The MIC of erythromycin, gentamicin and vancomycin for each of the indicator strains in the presence or absence of test compound is subsequently determined. The results observed are listed in Table 2 below.

TABLE 2

Augmentation Of The Antibacterial Activity Of Erythromycin MIC (µg/mL)

| Erythromycin plus: | E. coli 25922 | P. aeruginosa 27853 | P. aeruginosa 39324 |
|---|---|---|---|
| no compound | 125 | >250 | >250 |
| compound B* | <0.19 | 3.12 | 3.12 |
| compound D | 0.39 | 0.39 | 6.25 |
| compound H | <0.39 | 3.12 | 6.25 |
| compound J | 0.39 | 0.78 | 12.5 |
| compound N | 0.78 | 6.25 | 25 |

All compounds tested at 25 µg/mL, except compound H, which is tested at 6.25 µg/mL. Bacteria grow in CAMHB supplemented with each test compound at the indicated concentrations.

FIGS. 8A, 8B, 9A, 9B, 10A and 10B present selected results of the above-described augmentation experiments in the form of histograms. As shown in these figures, significant reductions in the MIC (µg/mL) of erythromycin are obtained with the co-administration of this conventional anti-infective agent with selected compounds of the formula. Comparable results are shown or expected for the other compounds of the formula.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

What is claimed is:

1. A method of treating an infection caused by an infectious microorganism comprising administering to a subject in need of such treatment an effective amount of a compound of the formula (I)

in which $R_1$ can be an H, OH, $OR_5$, $NH_2$, $NHR_6$ or $NR_6R_7$;

$R_2$ and $R_3$ may be the same or different and can be an H, OH or $OR_5$;

$R_4$ can be $CONH_2$, $CONHR_2$, $CONR_6R_7$, $CH_2NH_2$, $CH_2NHR_6$, $CH_2NR_6R_7$, $CO_2$—Y—$NH_2$, $CO_2$—Y—$NHR_6$, or $CO_2$—Y—$NR_6R_7$;

$R_5$ is a protected or unprotected glycosyl moiety comprising 1–10 monosaccharide units in which the glycosidic linkage at the anomeric carbon atom of each monosaccharide unit is independently alpha or beta;

$NH_2$, $NHR_6$, and $NR_6R_7$ represent an unsubstituted amino group, a monosubstituted amino group, and a disubstituted amino group, respectively, in which $R_6$ and $R_7$ may be the same or different and represent a hydrocarbon group comprising 1–15 carbon atoms substituted with one or more unsubstituted, monosubstituted or disubstituted amino groups;

Y represents a linear or branched alkylene group comprising 1–10 carbon atoms;

n is an integer from 0–10;

or its pharmaceutically acceptable salts;

provided that if $R_1$ is OH and $R_2$ is OH and $R_3$ is H, or if $R_1$ is OH and $R_2$ is H or OH and $R_3$ is OH, then $R_4$ cannot be a $CONH_2$, $CONHCH_2CH_2N(C_2H_5)_2$, $CON(CH_2CH_2)_2N$—$CH_3$, $CH_2NH_2$, $CH_2NHCH_2CH_2N(C_2H_5)_2$, or $CH_2CH_2)_2N$—$CH_3$ group.

2. The method of claim 1 in which the group $R_6$ together with the nitrogen atom to which it is attached represents a biogenic polyamine.

3. The method of claim 1 in which said compound can accommodate at least two positive charges.

4. The method of claim 1 in which said compound can accommodate at least three positive charges.

5. The method of claim 1 in which $R_6$ or $R_7$ represents 3-aminopropyl, 4-aminobutyl, 5-aminopentyl, N-(4-aminobutyl)-3-aminopropyl or N-[N-(3-aminopropyl)-4-aminobutyl]-3-aminopropyl.

6. The method of claim 1 in which $R_1$ has the configuration beta.

7. The method of claim 1 in which $R_1$ has the configuration alpha.

8. The method of claim 1 in which at least one of $R_1$, $R_2$, and $R_3$ represents OH.

9. The method of claim 1 in which at least two of $R_1$, $R_2$, and $R_3$ represent OH.

10. The method of claim 1 in which all three of $R_1$, $R_2$, and $R_3$ represent OH.

11. The method of claim 1 in which $R_1$ and $R_2$ represent $OR_5$, and $R_3$ represents OH.

12. The method of claim 1 in which $R_2$ and $R_3$ represent $OR_5$, and $R_1$ represents OH.

13. The method of claim 1 in which the group $R_7$ together with the nitrogen atom to which it is attached represents a biogenic polyamine.

14. The method of claim 1 in which said hydrocarbon group comprises a linear or branched aliphatic group.

15. The method of claim 1 in which said hydrocarbon group is cyclic.

16. The method of claim 1 in which said polyamine compound is a spermine.

17. The method of claim 1 in which said polyamine compound is a spermidine.

18. The method of claim 1 in which said compound comprises at least one $R_6$ group substituted with at least one unsubstituted amino group.

19. The method of claim 1 in which said subject is a plant.

20. The method of claim 1 in which said subject is an animal.

21. The method of claim 1 in which said subject is a human patient.

22. The method of claim 1 in which n=2.

23. The method of claim 1 in which $R_4$ is selected from the group consisting of CO-spermine, CO-pentamine, and CO-hexamine.

24. The method of claim 22 in which the compound is selected from the group consisting of $R_1$=α-OH, $R_2$=H, $R_3$=OH and $R_4$=CO-spermine;
$R_1$=α-OH, $R_2$=OH, $R_3$=OH and $R_4$=CO-spermine;
$R_1$=α-OH, $R_2$=c-D-Glc, $R_3$=a-D-Glc and $R_4$=CO-spermine;
$R_1$=α-OH, $R_2$=H, $R_3$=u-D-Glc and $R_4$=CO-spermine;
$R_1$=α-OH, $R_2$=c-D-Glc, $R_3$=H and $R_4$=CO-spermine;
$R_1$=α-OH, $R_2$=H, $R_3$=OH and $R_4$=CO-pentamine;
$R_1$=α-OH, $R_2$=H, $R_3$=OH and $R_4$=CO-hexamine;
$R_1$=α-OH, $R_2$=OH, $R_3$=H and $R_4$=CO-spermine;
$R_1$=α-OH, $R_2$=OH, $R_3$=H and $R_4$=CO-pentamine;
$R_1$=α-OH, $R_2$=OH, $R_3$=OH and $R_4$=CO-pentamine;
$R_1$=α-OH, $R_2$=OH, $R_3$=OH and $R_4$=CO-hexamine;
$R_1$=α-OH, $R_2$=α-D-Glc, $R_3$=α-D-Glc and $R_4$=CO-hexamine;
$R_1$=α-OH, $R_2$=α-D-Glc, $R_3$=α-D-Glc and $R_4$=CO-pentamine; and
$R_1$=α-OH, $R_2$=H, $R_3$=H and $R_4$=CO-hexamine.

25. A method for preventing or inhibiting the growth of at least one microorganism, comprising contacting a microorganism whose growth is to be prevented or inhibited with an effective amount of one or more compounds represented by the formula (I)

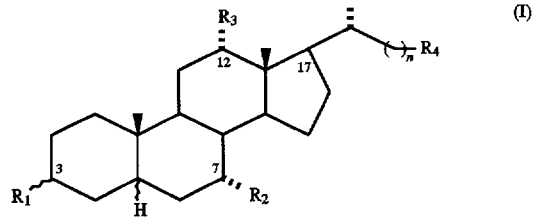

in which $R_1$ can be an H, OH, $OR_5$, $NH_2$, $NHR_6$ or $NR_6R_7$;

$R_2$ and $R_3$ may be the same or different and can be an H, OH or $OR_5$;

$R_4$ can be $CONH_2$, $CONHR_6$, $CONR_6R_7$, $CH_2NH_2$, $CH_2NHR_6$, $CH_2NR_6R_7$, $CO_2$—Y—$NH_2$, $CO_2$—Y—$NHR_6$, or $CO_2$—Y—$NR_6R_7$;

$R_5$ is a protected or unprotected glycosyl moiety comprising 1–10 monosaccharide units in which the glycosidic linkage at the anomeric carbon atom of each monosaccharide unit is independently alpha or beta;

$NH_2$, $NHR_6$, and $NR_6R_7$ represent an unsubstituted amino group, a monosubstituted amino group, and a disubstituted amino group, respectively, in which $R_6$ and $R_7$ may be the same or different and represent a hydrocarbon group comprising 1–15 carbon atoms substituted with one or more unsubstituted, monosubstituted or disubstituted amino groups;

Y represents a linear or branched alkylene group comprising 1–10 carbon atoms;

n is an integer from 0–10;

or its salts;

provided that if $R_1$ is OH and $R_2$ is OH and $R_3$ is H, or if $R_1$ is OH and $R_2$ is H or OH and $R_3$ is OH, then $R_4$ cannot be a $CONH_2$, $CONHCH_2CH_2N(C_2H_5)_2$, $CON(CH_2CH_2)_2N$—$CH_3$, $CH_2NH_2$, $CH_2NHCH_2CH_2N(C_2H_5)_2$, or $CH_2N(CH_2CH_2)_2N$—$CH_3$ group.

26. The method of claim 25, in which said microorganism is present on a surface of a surgical instrument.

27. The method of claim 25, in which said microorganism is present in a solid or liquid medium susceptible to microbial infestation.

* * * * *